(12) United States Patent
Bambot et al.

(10) Patent No.: US 9,561,003 B2
(45) Date of Patent: *Feb. 7, 2017

(54) METHOD AND APPARATUS FOR RAPID DETECTION AND DIAGNOSIS OF TISSUE ABNORMALITIES

(71) Applicant: Spectrx, Inc., Norcross, GA (US)

(72) Inventors: Shabbir Bakir Bambot, Duluth, GA (US); Mark Faupel, Alpharetta, GA (US); Jonathan David Mongin, Atlanta, GA (US)

(73) Assignee: Spectrx, Inc., Norcross, GA (US)

( * ) Notice: Subject to any disclaimer, the term of this patent is extended or adjusted under 35 U.S.C. 154(b) by 0 days.
This patent is subject to a terminal disclaimer.

(21) Appl. No.: 14/198,074

(22) Filed: Mar. 5, 2014

(65) Prior Publication Data

US 2015/0238135 A1 Aug. 27, 2015

Related U.S. Application Data

(63) Continuation of application No. 13/228,717, filed on Sep. 9, 2011, now Pat. No. 8,781,560, which is a continuation of application No. 11/601,904, filed on Nov. 20, 2006, now abandoned.

(60) Provisional application No. 60/737,949, filed on Nov. 18, 2005.

(51) Int. Cl.
| | | |
|---|---|---|
| *A61B 5/00* | (2006.01) | |
| *G01J 3/02* | (2006.01) | |
| *G01J 3/10* | (2006.01) | |
| *G01J 3/28* | (2006.01) | |
| *G01J 3/44* | (2006.01) | |
| *G01N 21/27* | (2006.01) | |
| *G01N 21/31* | (2006.01) | |
| *G01N 21/47* | (2006.01) | |
| *G01N 21/64* | (2006.01) | |
| *G01J 3/12* | (2006.01) | |

(52) U.S. Cl.
CPC ........... *A61B 5/4331* (2013.01); *A61B 5/0059* (2013.01); *A61B 5/0071* (2013.01); *A61B 5/0075* (2013.01); *A61B 5/0077* (2013.01); *G01J 3/02* (2013.01); *G01J 3/027* (2013.01); *G01J 3/0208* (2013.01); *G01J 3/0218* (2013.01); *G01J 3/0229* (2013.01); *G01J 3/0232* (2013.01); *G01J 3/0262* (2013.01); *G01J 3/0264* (2013.01); *G01J 3/0272* (2013.01); *G01J 3/0283* (2013.01); *G01J 3/0291* (2013.01); *G01J 3/10* (2013.01); *G01J 3/28* (2013.01); *G01J 3/4406* (2013.01); *G01N 21/274* (2013.01); *G01N 21/31* (2013.01); *G01N 21/474* (2013.01); *G01N 21/645* (2013.01); *G01J 2003/1213* (2013.01); *G01J 2003/2866* (2013.01); *G01N 2021/6417* (2013.01); *G01N 2021/6423* (2013.01); *G01N 2021/6484* (2013.01); *G01N 2201/0221* (2013.01)

(58) Field of Classification Search
CPC .................................................... A61B 5/0059
USPC ......................................... 600/407, 473–476
See application file for complete search history.

(56) References Cited

U.S. PATENT DOCUMENTS 5,813,987 A 9/1998 Modell et al.
6,104,945 A 8/2000 Modell et al.
(Continued)

*Primary Examiner* — Peter Luong
(74) *Attorney, Agent, or Firm* — Altera Law Group, LLC

(57) ABSTRACT

A method and apparatus are provided that interrogate, receive, and analyze full emission spectra for at least one fluorescence excitation wavelength and for at least one reflectance measurement to determine tissue characteristics and correlate same to photographic images. Further, the system and method accomplish this measurement rapidly by increasing the light throughput by integrating optics into a hand held unit and avoiding the need for a coherent fiber optic bundle being used. The method includes illuminating a first portion of a target tissue with optical energy, forming a first image of the target tissue, illuminating a second portion of the target tissue with optical energy, performing spectroscopic measurements on optical energy reflected and/or emitted by the target tissue upon illumination of the second portion of the target tissue with optical energy, and determining tissue characteristics of the target tissue based on the results of the spectroscopic measurements.

20 Claims, 35 Drawing Sheets

(56) References Cited

U.S. PATENT DOCUMENTS

| | | |
|---|---|---|
| 6,148,223 A | 11/2000 | Davis et al. |
| 6,192,734 B1 | 2/2001 | Rothfritz et al. |
| 6,364,829 B1 | 4/2002 | Fulghum |
| 6,411,835 B1 | 6/2002 | Modell et al. |
| 6,411,838 B1 | 6/2002 | Nordstrom et al. |
| 6,571,118 B1 | 5/2003 | Utzinger et al. |
| 6,760,613 B2 | 7/2004 | Nordstrom et al. |
| 6,826,422 B1 | 11/2004 | Modell et al. |
| 7,469,160 B2 | 12/2008 | Banks et al. |
| 2001/0047136 A1 | 11/2001 | Domanik et al. |
| 2002/0045831 A1 | 4/2002 | Wake et al. |
| 2002/0065468 A1 | 5/2002 | Utzinger et al. |
| 2006/0184037 A1 | 8/2006 | Ince et al. |

| # | Measurement | Excitation | Collection | Spectrograph center λ | Meas. time secs. |
|---|---|---|---|---|---|
| 1 | Flourescence | 350 nm (10 nm BP) | 385 nm LP (GG 385) | 450nm | 2 |
| 2 | Flourescence | 400 nm (10 nm BP) | 420 nm LP (GG 485) | 500nm | 2 |
| 3 | Flourescence | 460 nm (10 nm BP) | 495 nm LP (GG 495) | 560nm | 4 |
| 4 | Reflectance | OD1.5 ND filter | 300-700 nm bp (BG 26) | 500nm | 0.2 |

BP=bandpass
LP=Long-pass

| Measurement | Mask Position | Exposure Time | Excitation Filter | Spectrograph Center λ | Collection Filter | Safety Shutter Open |
|---|---|---|---|---|---|---|
| 1 | 1 | 0.2 | ND 1.5 | 580 | WG-320 | No |
| 2 | 2 | 0.2 | ND 1.5 | 560 | WG-320 | No |
| 3 | 3 | 0.2 | ND 1.5 | 540 | WG-320 | No |
| 4 | 4 | 0.2 | ND 1.5 | 520 | WG-320 | No |
| 5 | 5 | 0.2 | ND 1.5 | 500 | WG-320 | No |
| 6 | 6 | 0.2 | ND 1.5 | 480 | WG-320 | No |
| 7 | 7 | 0.2 | ND 1.5 | 460 | WG-320 | No |
| 8 | 8 | 0.2 | ND 1.5 | 440 | WG-320 | No |

FIG. 22

| Measurement | Mask Position | Exposure Time | Excitation Filter | Spectrograph Center λ | Collection Filter | Safety Shutter Open |
|---|---|---|---|---|---|---|
| 1 | 1 | 0.2 | ND 1.5 | 580 | WG-320 | No |
| 2 | 1 | 0.2 | ND 1.5 | 580 | WG-320 | Yes |
| 3 | 2 | 0.2 | ND 1.5 | 560 | WG-320 | Yes |
| 4 | 3 | 0.2 | ND 1.5 | 540 | WG-320 | Yes |
| 5 | 4 | 0.2 | ND 1.5 | 520 | WG-320 | Yes |
| 6 | 5 | 0.2 | ND 1.5 | 500 | WG-320 | Yes |
| 7 | 6 | 0.2 | ND 1.5 | 480 | WG-320 | Yes |
| 8 | 7 | 0.2 | ND 1.5 | 460 | WG-320 | Yes |
| 9 | 8 | 0.2 | ND 1.5 | 440 | WG-320 | Yes |

FIG. 23

| Measurement | Mask Position | Exposure Time | Excitation Filter | Spectrograph Center λ | Collection Filter | Safety Shutter Open |
|---|---|---|---|---|---|---|
| 1 | 1 | 4 | 350-20 | 580 | GG385 | No |
| 2 | 1 | 4 | 350-20 | 580 | GG385 | Yes |
| 3 | 2 | 4 | 350-20 | 560 | GG385 | Yes |
| 4 | 3 | 4 | 350-20 | 540 | GG385 | Yes |
| 5 | 4 | 4 | 350-20 | 520 | GG385 | Yes |
| 6 | 5 | 4 | 350-20 | 500 | GG385 | Yes |
| 7 | 6 | 4 | 350-20 | 480 | GG385 | Yes |
| 8 | 7 | 4 | 350-20 | 460 | GG385 | Yes |
| 9 | 8 | 4 | 350-20 | 440 | GG385 | Yes |
| 10 | 1 | 2 | 400-20 | 580 | GG435 | No |
| 11 | 1 | 2 | 400-20 | 580 | GG435 | Yes |
| 12 | 2 | 2 | 400-20 | 560 | GG435 | Yes |
| 13 | 3 | 2 | 400-20 | 540 | GG435 | Yes |
| 14 | 4 | 2 | 400-20 | 520 | GG435 | Yes |
| 15 | 5 | 2 | 400-20 | 500 | GG435 | Yes |
| 16 | 6 | 2 | 400-20 | 480 | GG435 | Yes |
| 17 | 7 | 2 | 400-20 | 460 | GG435 | Yes |
| 18 | 8 | 2 | 400-20 | 440 | GG435 | Yes |
| 19 | 1 | 2 | 460-20 | 580 | GG495 | No |
| 20 | 1 | 2 | 460-20 | 580 | GG495 | Yes |
| 21 | 2 | 2 | 460-20 | 560 | GG495 | Yes |
| 22 | 3 | 2 | 460-20 | 540 | GG495 | Yes |
| 23 | 4 | 2 | 460-20 | 520 | GG495 | Yes |
| 24 | 5 | 2 | 460-20 | 500 | GG495 | Yes |
| 25 | 6 | 2 | 460-20 | 480 | GG495 | Yes |
| 26 | 7 | 2 | 460-20 | 460 | GG495 | Yes |
| 27 | 8 | 2 | 460-20 | 440 | GG495 | Yes |

FIG. 24

US 9,561,003 B2

METHOD AND APPARATUS FOR RAPID DETECTION AND DIAGNOSIS OF TISSUE ABNORMALITIES

CROSS REFERENCE TO RELATED APPLICATIONS

This application is a continuation of patent application Ser. No. 13/288,717 filed on 9 Sep. 2011 which is now U.S. Pat. No. 8,781,560 which is a continuation of patent application Ser. No. 11/601,904 filed on 20 Nov. 2006 which is now abandoned which claims the benefit of U.S. Provisional Application No. 60/737,949 filed 18 Nov. 2005 hereby is incorporated herein by reference in its entirety.

FIELD OF THE INVENTION

The invention relates to medical diagnostics, more particularly, identification of normal and diseased tissue.

BACKGROUND

Cervical Cancer is the second most common type of cancer in women worldwide and the leading cause of cancer related mortality in women in developing countries. Early detection and diagnosis can saves lives and reduce the burden on the national healthcare system. We have built a non-invasive research-prototype point-of-care device to detect early cancerous conditions of the uterine cervix. We have tested this prototype in a multi-center national study accruing data from 600 women for training our algorithm. Through conversations with the FDA we now have in place a pivotal trial protocol for validating our algorithm. We will use a pre-production version of our device in this pivotal study. The pre-production device is will be a cost and size reduced, portable, rugged and user-friendlier device and is intended to be identical to the device intended for sale without incurring the tooling costs necessary to enter the production phase.

Epithelial cancers collectively constitute about 90% of all cancer occurrences. Common epithelial cancers include skin, cervical, GI tract, colon and oral cancer. While the technology we have developed is generic and applicable to any accessible epithelial cancer, we have chosen cervical cancer as our first diagnostic target. This is because the cervix is easily accessible and the pathophysiology of cancer progression in it is well understood. Cervical cancer is a leading cause of cancer-related mortality in women in developing countries and the second most common type of cancer in women worldwide. The American Cancer Society estimates that there will be 12,200 new cases of invasive cervical cancer diagnosed in 2003 and about 4,100 women will die from the disease in the US this year. Worldwide, there are approximately 500,000 cases of cervical cancer diagnosed annually and approximately 230,000 deaths per year. Estimates show the market potential for non-invasive cervical cancer detection to be at $1.25 billion annually in the US and Europe.

Cervical cancer screening: The Pap test is currently the most widely used tool to screen women for cervical cancer or neoplasia. While its contribution to reducing patient mortality is widely acknowledged, it is prone to errors from low screening frequency, insufficient cell sampling, inadequate sample preparation, lack of exfoliation of abnormal cells, and technician reading error. The discrimination performance of this test is therefore limited, resulting in a tradeoff between sensitivity and specificity as illustrated in a landmark meta-analysis conducted by Fahey. Current practice sets the sensitivity at 51% in order to achieve a specificity of 97%. Thus, Pap tests have been used as a means to 'rule out' rather than 'rule in' disease. One rationale behind this is to limit the large number of false positives that would inadvertently burden downstream health management systems. While this may be true, this also results in a deference of diagnosis at an annual cost of nearly $2 billion. Improvements to the traditional Pap test such as ThinPrep® are becoming increasingly popular with physicians. This test contributes to lower intermediate classifications such as ASCUS and increases the percentage of LSIL+ patients sent to colposcopy. Using a different approach, the Digene HPV test used for ASCUS triage appears to be better than a repeat Pap test in finding patients with CIN3 who are referred to colposcopy. In a recent study of 8,170 screened women HPV detected 93.3% of CIN3. However, the sensitivity for CIN2 disease was only 72% so that the overall sensitivity of HPV for HSIL (CIN 2/3 and higher) was 81.8%. Moreover, a low-test specificity results in an increase in false positives. Also, while the FDA has approved computerized aids to Pap test screening such as AutoPap and Papnet, the evidence regarding the impact of these technologies on the screening process is not yet available.

Cervical cancer diagnosis: A positive first or second Pap test is followed by a colposcopic examination. This involves visualization of the cervix under low power magnification by a trained clinician who looks for visual cues attributable to neoplasia. The clinician then takes a tissue biopsy from that location. The amount of tissue biopsied varies according to the extent of the assessed lesion and, in some cases, the entire cervix is removed in what is known as a Loop Electrosurgical Excision Procedure (LEEP). A pathologist whose diagnosis is considered the gold standard examines the biopsy specimens. Since suspect areas are identified visually, colposcopy requires extensive training, experience, and a significant effort toward maintenance of skills.

A key disadvantage of the current methods is the significant time delay in obtaining the results. A patient and care provider must wait 1-4 weeks for the results of the Pap test. Quite often the colposcopy, biopsy and histology sequence has to be repeated in order to localize and diagnose the disease definitively. A point of care approach in new technology will be a significant advantage.

The problem is further compounded by the performance limits of colposcopy. A meta-analysis of colposcopy summarizing the results of 9 studies lists the average sensitivity and specificity at 85% and 69% respectively for separating LSIL and lower (CIN 1 and lower) from HSIL (CIN 2/3 and higher). More recent studies show a much lower sensitivities of 53% and 56%.

Therefore, a strong need clearly exists for better differentiation at any point along the entire screening to diagnosis path. The low specificity and sensitivity numbers result in a large number of patients undergoing unnecessary biopsy and/or a large number of patients with cancer going untreated. Moreover, the one to four weeks required to obtain a Pap test result or a histology evaluation results in increased patient anxiety and/or reduced patient commitment to seeking aggressive treatment. This is especially problematic in treating patients in developing countries and with indigent populations in the US and other developed countries. Given that these are the same populations with the highest prevalence of cervical disease, a point-of-care approach would have greater value in overall disease management. Similar approaches have successfully emerged in other areas of diagnosis and testing such as 'stat' blood gas and blood chemistry analysis as well as in home immunochemistry assays. In addition there is a need for a less traumatic diagnostic method.

SUMMARY

The present invention is directed to improvements on non-contact methods of diagnosing tissue abnormalities preferably by optical methods. Reference should be had to the detailed description and the claims for complete disclosures.

BRIEF DESCRIPTION OF THE FIGURES

The invention will be described in detail with reference to the following drawings, in which like reference numerals refer to like elements, and wherein:

FIGS. 22-23 are tables of instrument settings for each of eight software driven measurements that account for each of eight column positions on a target;

FIG. 24 is a table of instrument settings for measurements made in three sets using a different excitation and emission wavelength for each set.

Before the present systems, methods and apparatus are disclosed and described, it is to be understood that the terminology used herein is for the purpose of describing particular embodiments only and is not intended to be limiting. It must be noted that, as used in the specification and the appended claims, the singular forms "a", "an" and "the" include plural referents unless the context clearly dictates otherwise.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

Quantitative optical spectroscopy improves on prior art technology in the four major areas listed below. If realized, these can solve the majority of problems that exist with cervical cancer care.

Various embodiments of the present invention include systems, methods and apparatus that may be utilized to determine tissue characteristics by applying and measuring optical energy, including but not limited to visible, infrared and/or UV light. It should be understood that the term "illumination" according to the invention means "to give optical energy to", the term optical energy again, including but not limited to visible, infrared and/or UV light.

In several embodiments, the present invention comprises a base unit, a tissue interface unit and a pathway that couples the base unit and the tissue interface unit. In one particular embodiment, the present invention is comprised of a tissue interface unit that is optically and electronically coupled to a base unit, as shown in FIGS. 1A-1B.

Figure 1A:
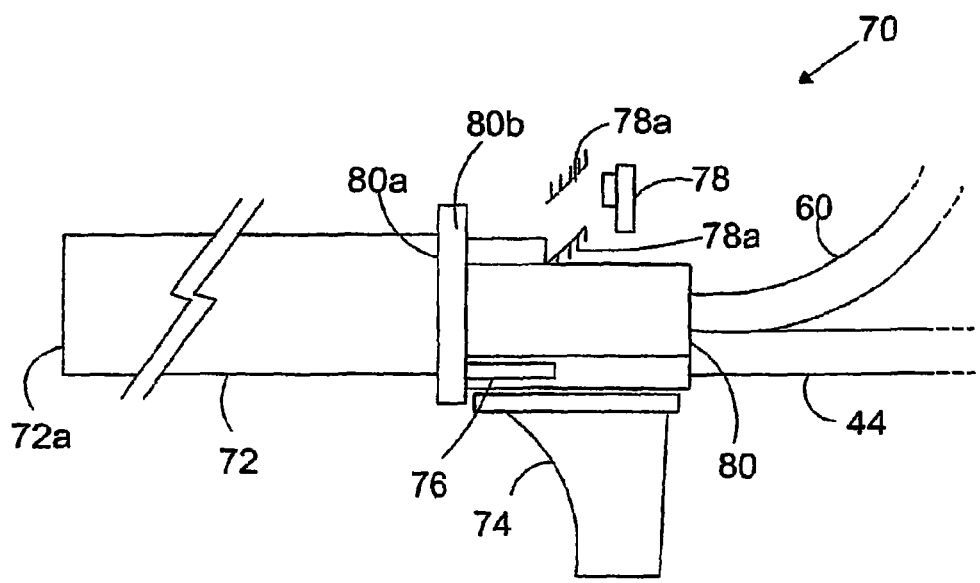
FIG. 1A is a schematic side view of a tissue interface unit of a system for determining tissue characteristics according to one embodiment of the invention.
Figure 1B:
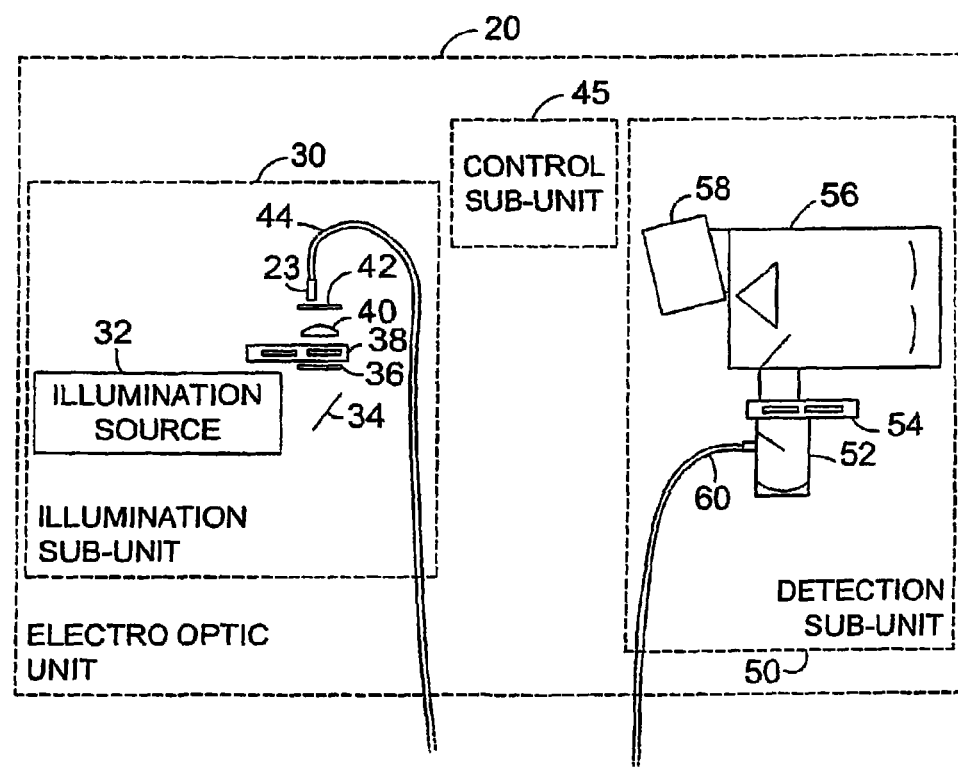
FIG. 1B is a schematic diagram of a base unit of a system for determining tissue characteristics according to one embodiment of the invention.

FIG. 1A is a schematic side view drawing of a tissue interface unit according to an embodiment of the present invention. The tissue interface unit 70 includes a base structure 80. The base structure 80 may include a handle 74 attached thereto and configured to be graspable by a user; however, other configurations may also be appropriate.

A tube 72 may be configured to be removably attachable to the base structure 80. The tube 72 functions as a barrier to exclude, for example, room light. The tube 72 is not necessarily tubular or cylindrical in shape; other configurations may also be appropriate.

Figure 2:
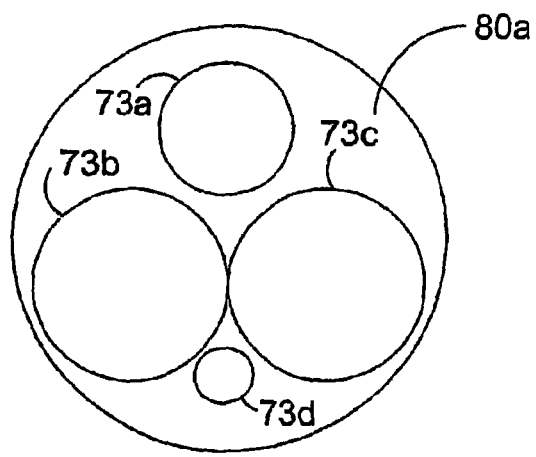
FIG. 2 is a front view of an end plate of a body structure of the tissue interface unit of FIG. 1A.

The tube 79 connects to base structure 80 via plate 80b. An end face 80a of plate 80b is shown in FIG. 2. The end face 80a contains at least one opening for respective pathways 73a, 73b, 73c, 73d. These pathways are connected to and selectively share the tube 72 in such a way that no interference occurs between the respective pathways. For example, illumination pathway 73b delivers to a subject tissue illumination energy or light received from the base unit 20 along illumination pathway 44. The collection pathway 73c receives energy or light reflected and/or emitted by a subject tissue and guides it to collection pathway 60, which guides the collected light to the base unit 20.

The tissue interface unit 70 may further include an illumination source 76 and a second illumination pathway 73d. Additionally, the tissue interface unit 70 may include an imaging device 78 and an imaging pathway 73a. The imaging device could take the form of a digital camera, or a CCD based imaging device, although other imaging devices could also be used. The second illumination pathway 73d delivers illumination energy or light from the illumination source 76 to the subject tissue. This illumination energy or light is reflected off the subject tissue as image energy or light. The image energy or light is received into the imaging pathway 73a where it is directed to an imaging device 78. The imaging device is then used to provide a user with an image of all or a portion of the subject tissue.

The second illumination pathway 73d and the imaging device 7S comprise the imaging channel (not shown). The imaging device 78 allows the user to position the distal end 72a of the tube 72 in the proper and otherwise desired contact with the tissue and to verify that such contact has been accomplished. Moreover, the imaging channel allows the user to acquire a digital or other image of the tissue with the help of the imaging device 78. This image can serve as an additional visual tissue diagnosis tool.

The tissue interface unit 70 may also contain various lens assemblies (not shown) that direct optical energy from the illumination pathways 73b, 73d onto the subject tissue, and that direct energy or light from the subject tissue into the collection pathway 73c and the imaging pathway 73a. For example, the various lens assemblies may comprise a set of achromatic lens doublets. The matched set of achromatic lens doublets may be provided in each pathway. The doublets are generally those commonly used in the art, such as a $BK^7/SF^2$ glass biconvex/planoconcave combination available off the shelf from Edmund Scientific, OptoSigma and Melles Griot; although other lenses may also be appropriate. The material of the lenses may be used to limit irradiation and collection in the UV to a desired wavelength range, such as for example a minimum wavelength of approximately 350 nm wavelength range. According to embodiments of the present invention, the lenses may provide magnification/demagnification in the excitation/collection paths, respectively.

The tube 72 can function to fix the lens assemblies a predetermined distance from the subject tissue. In addition, if the subject tissue is surrounded by the end 72a of the tube 72, the tube can function to exclude ambient optical energy from illuminating the subject tissue. The tube makes contact with the tissue setting the focal distance so the tissue to lens distance is correct.

Figure 1C:
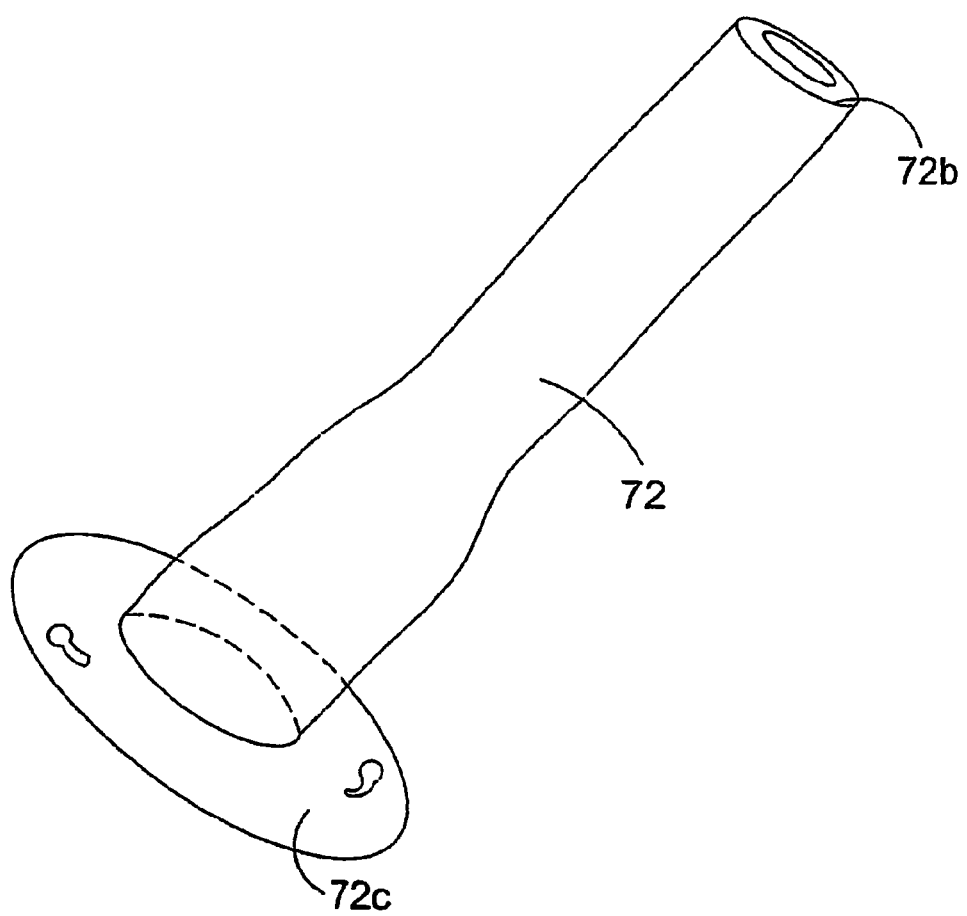
FIG. 1C is a schematic diagram of a tube according to one embodiment of the invention having a clear annulus at a distal end thereof.

The illumination pathway 73b may include, for example, a custom designed bundle of optical fibers. In one example, 52 optical fibers approximately 2 meters long, having a numerical aperture (NA) of approximately 0.12, and having a core diameter of approximately 100 .mu.m is utilized to form the illumination pathway 73b. This fiber bundle may be only part of the illumination pathway. The illumination pathway may also have lenses. According to one embodiment, the tube 72 comprises a clear annulus 72b at a distal end thereof opposite to an end plate 72c that allows the tube 72 to be attached, removably according to certain embodiments, to the base structure 80, as shown in FIG. 1C. Contact of the tube 72 to the surface of the tissue will be visible through the annulus 72b, which provides the user with visual confirmation that the tube 72 is properly positioned.

Figures 3, 6:
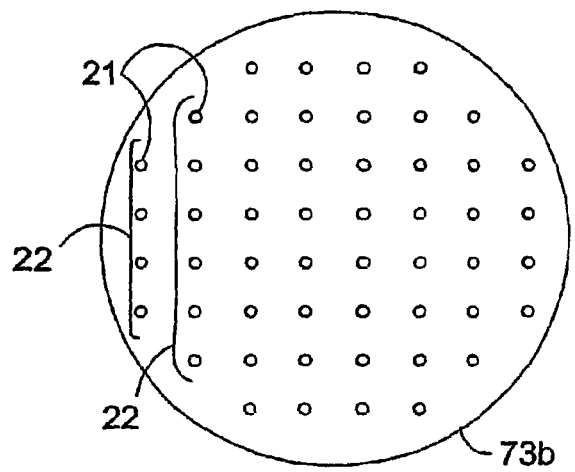
FIG. 3 shows an exemplary arrangement of illumination optical fibers on an end plate of a body structure of a tissue interface unit according to one embodiment of the invention.
FIG. 6 is a chart of exemplary spectrographic measurements to be taken to determine tissue characteristics according to one embodiment of the invention.
Figure 4:
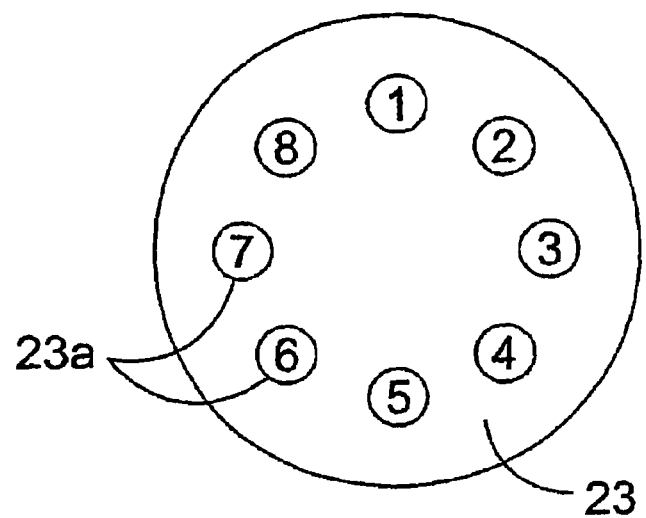
FIG. 4 shows an exemplary arrangement of bundles of optical fibers located at one end of an illumination pathway adjacent an illumination unit according to one embodiment of the invention.

One exemplary arrangement of optical fibers is illustrated in FIG. 3. The tissue end of the optical fiber bundle is held in the tissue interface unit 70 behind a pair of achromatic lens doublets (not shown). At the tissue end, the optical fibers 21 are arranged as shown in FIG. 3, in 8 columns 22. At the opposite end of the illumination pathway 44, the optical fibers 21 for each column 22 shown in FIG. 3 may be collected into a separate bundle 23a, as shown in FIG. 4. This means that there will be eight bundles 23 of optical fibers 21 at the opposite end of the illumination pathway.

When constructed in this manner, if optical energy is fed into a single bundle 23a at a time, a single column 22 of optical fibers 21 will illuminate the target tissue, as discussed below in detail.

The collection pathway 73c may be, for example, another custom designed coherent bundle of optical fibers. In one example, several thousand, e.g. 5000, optical fibers that were approximately 2 meters long, having a NA of approximately 0.12, and having a core diameter of approximately 50 µm were arranged in an approximately 5-mm diameter aperture, in a coherent fashion, to provide a one to one image transfer from the tissue interface unit to the detection sub-unit of the base unit. The tissue end of the bundle of optical fibers is held in the tissue interface unit behind a pair of achromatic lens doublets. Since one column of spots is illuminated on the tissue, for example, cervix, at a time, as is later discussed, returned radiation from the same column is transferred by the coherent bundle to the detection sub-unit of the base unit. This returned radiation, which will be arranged in a column of spots, acts as a virtual vertical slit that is then spectrally resolved in the horizontal dimension by the detection sub-unit of the base unit, as is later discussed.

As mentioned above, some embodiments of the device may include an illumination device 76 and image detector 78. Together, these items allow the device operator to obtain a real-time image of the target tissue, which can help to properly orient the tissue interface unit with respect to the target tissue. These items are not required in all embodiment of the invention, and could be completely eliminated. In other embodiments of the invention, these items could be replaced with a sighting mechanism which simply allows the device operator to look down the tube 72 to view the target tissue.

In embodiments of the invention that include an illumination device 76 and imaging device 78, the illumination source 76 may be, for example, a 4.25V or 2 W halogen lamp manufactured by Welch Allyn, Inc. in Skeneateles, N.Y. This exemplary lamp has an integrated parabolic reflector that projects the optical energy onto the tissue and provides a uniform illumination on the tissue. The imaging device 78 may be, for example, a ¼" format Panasonic color board camera with 480 horizontal TV lines. This camera has a C mount adaptor, into which a focusing lens doublet may be mounted. The camera may be mounted offset from the illumination and collection pathways due to space constraints, and the image transfer accomplished using a pair of reflectors 78a.

The tissue interface unit may be designed in conjunction with a vaginal speculum configured for insertion into a patient's vagina during the examination procedure. The unit is held fixed with respect to the vaginal speculum (not shown) according to certain embodiments. However, according to other embodiments, the unit may be used without such a speculum.

Prior to conducting tissue measurements, some embodiments of the instrument may be calibrated by malting one or more measurements on a disposable calibration target 78a that mounts on the distal tissue end of the tube 72. This disposable calibration target could be used to take a reference or a calibration measurement, or possibly both. Moreover, in various embodiments, these measurements may be a reflectance and/or fluorescent measurements.

FIG. 1B is a schematic diagram of a base unit according to one embodiment of the invention. The base unit 20 according to the invention is small enough to be portable or mobile. For example, the base unit 20 could be provided on a movable cart (not shown).

The base unit 20 comprises an illumination sub-unit 30, a detection sub-unit 50 and a control sub-unit 45. The illumination sub-unit 30 includes an illumination source 32. For example, the illumination source may be a 175 W short arc Xe lamp provided with an integrated parabolic reflector, which produces a near collimated beam. Such a lamp is manufactured by ORC lighting products, a division of PerkinElmer Optoelectronics (Azusa, Calif.). Other lamps may also be appropriate. In addition, the illumination source 32 could also take the form of one or more lasers or LEDs. The illumination source 32 may be housed inside a fan cooled heat sink assembly (not shown) to limit dissipation of heat to the illumination sub-unit's other components.

Optically coupled to the illumination source 32 is an illumination filter wheel 38. The illumination filter wheel 38 provides for selective wavelength filtering and may be motorized. For example, the illumination filter wheel may be an eight-position filter wheel manufactured by ISI Systems (Santa Barbara, Calif.). An example of filters that could be used in one embodiment of the invention are listed in FIG. 6. The illumination filter wheel is mounted within the illumination sub-unit 30, as shown in FIG. 5B, and the control unit 45 selects the appropriate filter to be brought into the light path.

A cold mirror 34 may be provided between the illumination source 32 and the illumination filter wheel 38. In another embodiment of the invention, an IR absorbing glass/filter may be used instead of a cold mirror. A near collimated light beam from the illumination source 32 is directed through the filter. For example, in one embodiment of the invention, Applicants utilized a KGI glass filter available off the shelf from Melles Griot. The filter transmitted wavelengths in the range of approximately 340-700 nm. Because of its high absorption of IR wavelengths, the filter helps protect downstream components from excessive heat and also minimizes stray light in the detection sub-unit.

The illumination sub-unit 30 may also include a safety shutter 36, in particular where a continuously operating illumination source is utilized. In such a case, illumination would only be allowed into the unit and through to the tissue for the duration of the spectroscopic measurements, even though the illumination source would be continuously operating. Software in the control unit 45 would control actuation of the normally closed shutter.

The illumination sub-unit 30 may also include a focusing lens 40, for example, a single approximately 28 mm diameter, approximately 100 mm FL, plano-convex lens. The focusing lens 40 focuses the illumination optical energy or light onto the illumination pathway 44.

A mask 42, motorized using an encoded stepper motor (not shown) and controlled by the control sub-unit 45, may be provided at an entrance to the illumination pathway 44. The mask 42 is used to control the optical energy so that the optical energy will only pass into certain portions of the illumination pathway, for example, into certain ones of the optical fibers, at any given time. The mask 42 blocks the illumination optical energy from entering the remaining portions of the illumination pathway, for example, certain remaining optical fibers.

Figure 5:
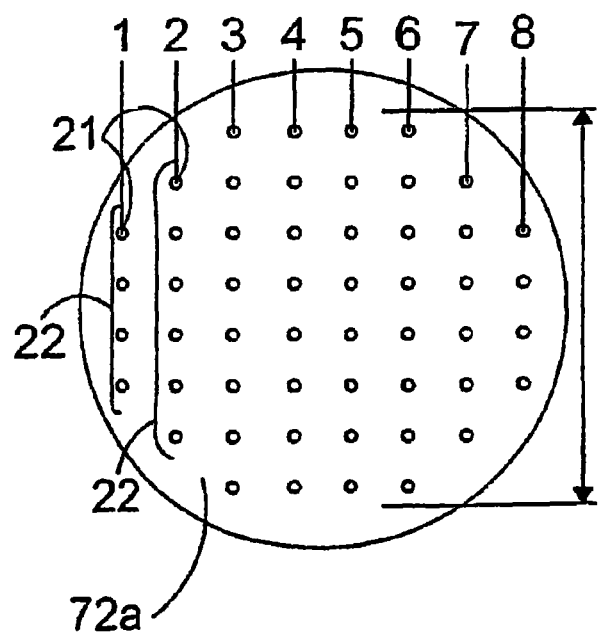
FIG. 5 shows an exemplary columnar arrangement of illumination optical fibers on an end plate of a body structure of a tissue interface unit according to one embodiment of the invention.

By way of an example, one embodiment of the illumination sub-unit end 23 of the illumination pathway 44 is shown in FIG. 4. As previously discussed, it has a collection of eight bundles 23a of optical fibers, where the optical fibers in each bundle 23a corresponding to different respective columns 22 of individual optical fibers at the tissue end 80a of the illumination pathway 44, as shown in FIG. 5. Thus, the optical fibers in bundle number 1 at the illumination sub-unit end of the illumination pathway 44, as shown in FIG. 4, correspond to the optical fibers 21 arranged in column 1 of the tissue end 80a, as shown in FIG. 5.

The mask 42 has a single hole (not shown) that can be selectively aligned with only a single bundle 23a of the optical fibers shown in FIG. 4. The control sub-unit 45 will control movement of the mask 42 so that each bundle 23, in turn, is illuminated. This will cause the illumination optical energy to be emitted from one of the columns 22 shown in FIG. 5, and as the mask 42 moves, different ones of the columns 22 of optical fibers will illuminate the target tissue.

The detection sub-unit 50 may comprise a re-imaging device 52, a collection filter wheel 54, a spectrograph 56 and a CCD camera 58. The collection filter wheel 54 is optically coupled to the spectrograph and holds a plurality of filters (not shown) for filtering the collected optical energy before it is sent into the spectrograph 56. Exemplary filters for multiple spectral measurements are listed in FIG. 6. Filtering can be used to reduce artifacts due to reflected excitation from the target tissue. When attempting to measure fluorescent emissions from the target tissue, which have a very low amplitude, a reduction in the reflected excitation energy or light amount is quite helpful. The insertion of filters, however, can change the light path between the optical fibers and the spectrograph entrance slit.

The collected optical energy, which has traveled through, for example, optical fibers to the detection sub-unit, is re-imaged at the entrance slit of the spectrograph 56 by a re-imaging device 52, such as, for example, an FC446-30 from Roper Scientific-Acton Research (Acton Mass.), which does this without introducing chromatic aberrations and astigmatism. Such a re-imaging device may include a spacer (not shown) which allows insertion of a motorized collection filter wheel, such as, for example, an FA-448-2 filter wheel also from Roper Scientific-Acton Research. The re-imaging device permits simple, straightforward insertion of the filter wheel.

The collection pathway 60, which may be, for example, a coherent bundle of optical fibers 60, which carries optical energy collected from the target tissue, is placed at the entrance of the re-imaging assembly. At any given time, the illumination pathway 44, which may be, for example, optical fibers, will only illuminate a column of positions on the target tissue. Thus, optical energy collected into the collection pathway 60 will only be from approximately the same column of positions on the target tissue. The result is that, at any given time, the optical energy entering the spectrograph 56 from the return optical fibers 60, will be arranged in a virtual vertical slit.

The spectrograph 56 takes the vertical slit of returned optical energy, and resolves the optical energy into different wavelengths by separating the energy or light in the horizontal direction. The result is an energy or light pattern having two dimensions, wherein the vertical dimension corresponds to different positions on the target tissue, and wherein the horizontal dimension corresponds to different wavelengths. The two dimensional energy or light pattern is then recorded on a camera, for example, a CCD camera 58.

The spectrograph may be, for example, a customized, approximately 300 mm focal length, f#4, Czerny-Turner configuration spectrograph, such as the SpectraPro SP-306I, manufactured by Roper Scientific-Acton Research (Acton Mass.). According to one embodiment of the invention, the grating of the spectrograph has the following specifications:

Grooves/mm: 100 nm/mm
Dispersion: 32 nm/mm
Blaze angle: 1 17'
Field of view: 365 nm The camera may be a CCD camera, for example, a thermoelectrically cooled CCD camera, such as the NTE/CCD-512SB manufactured by Roper Scientific-Princeton Instruments (Princeton, N.J.) with a SITE 512×512, square format, approximately 24 m pixel, back illuminated detector, along with the ST-133 high speed DMA serial interface controller. The A/D converter in the controller allows a 1.0 MHZ A/D scan rate. However, other types of cameras commonly known to those skilled in the art may be used.

In one embodiment, the control unit 45 is a software/hardware package comprised of an instrument control section, a graphical user interface, and data storage capabilities. For example, a compact PC with adequate ports and bays to accommodate the requisite interfaces and PCI cards may be used for this purpose. The control unit 45 provides control over actuation of the illumination and collection filter wheels 38, 54, the safety shutter 36, the camera shutter (not shown), the camera controller (not shown), data conversion and transfer to the PC (not shown), the spectrograph grating adjust motor (not shown), the imaging camera 68 and corresponding illumination source 32 and the stepper motor (not shown) for the motorized mask. Control is provided according to a schedule template that can be modified by the user.

In addition, the software may provide graphical feedback to the user showing images (video and spectroscopy) that are used to make real time determinations of measurement adequacy. The program stores the measured data, which may include tissue particulars, measurement particulars and/or images. The measured data for each tissue can then be downloaded and stored in a portable recording medium (not shown) such as a magnetic or optical disk.

The above described embodiment, which includes a spectrograph for spectrally resolving the light returning from the target tissue, is but one way to accomplish the spectral resolution. In other embodiments of the invention, other devices such as prisms or transmissive gratings, for example, could be utilized to spectrally resolve light returning from a location on a target tissue into different wavelengths. Yet, even further, other devices known to those of ordinary skill in the art could be utilized. For purposes of discussion and example only, a spectrograph will be discussed as the spectrally resolution device.

In addition, in some embodiments of the device, it may prove more advantageous to take measurements at a plurality of locations on a target tissue to measure a single narrow wavelength band of returned light during a first measurement cycle. Another measurement cycle could then be conducted at the same locations on the target tissue for one or more different wavelength bands.

Furthermore, in the embodiment described above, the illumination light was conveyed to the target tissue such that it sequentially illuminated several different columns of positions on the target tissue. In other embodiments of the invention, the illuminated positions on the target tissue need not be illuminated in a column arrangement. In fact, it some embodiments of the invention) it may be advantageous to arrange the optical fibers such that each sequential illumination and measurement cycle measures the characteristics of widely separated locations across the target tissue. Once all measurements have been taken, the measurement results could be re-combined by the device operating software to present an image indicative of the target tissue characteristics. A device configured in this manner would greatly reduce the occurrence of cross-talk between illuminated positions.

The systems, methods and apparatus according to the present invention use the hyperspectral imaging approach discussed by J. Marno in "Hyperspectral imager will view many colors of earth," Laser Focus World, August 1996, p. 85. This involves measuring intensities of optical energy emitted from tissue at high spectral and spatial resolution.

Systems, methods and apparatuses embodying the present invention should be designed to ensure that, as between measurement speed, spectral resolution, and spatial resolution, the most important characteristics are measured with the highest resolution in the shortest possible time period.

In order to obtain spectra free of environmental or system artifacts, one approach would be to calibrate the system embodied by the present invention. The calibration procedures are as follows: (1) provide an absolute scale to the intensity measurements at each wavelength; (2) provide an absolute wavelength scale; (3) correct for fluctuations in lamp intensity and spectral shifts; (4) correct for spectrograph/grating performance limitations due to stray light; (5) correct for background light; (6) correct for noise; and/or (7) correct for variance and temporal changes in optical properties, spectral transmittance, reflectance lenses and fibers. Providing an absolute scale to the intensity measurements at each wavelength calibrates the detection elements of the system and provides an absolute scale to the intensity measurements. This will also allow identification of performance variations in the source and detection system.

With respect to noise, there exists categories of potential noise that might typically occur with measurements comes from several possible sources. Without limitation, they include shot noise, instrument noise, clinical noise, and physiological noise.

Shot noise is equal to $\sqrt{I}$ and refers to the inherent natural variation of the incident photon flux. Photoelectrons collected by a CCD exhibit a Poisson distribution which have this square root relationship between signal and noise. Instrument noise includes several individual noise types classified according to their sources such as CCD noise including the read noise and dark noise and dependent on the A/D transfer rates and the temperature of the CCD, respectively. Additional sources of instrument noise include, without limitation, variability in lamp intensity, variability in the transmittance of optical components such as fibers filters and lenses, and variability in the transmittance of fibers due to fiber bending.

Clinical noise is the noise that arises from the clinical measurement procedure such as the distance/angle between the target tissue and the device, presence of blood and mucus as well as patient/device movement.

Physiological noise is the non-diagnostic natural variability of the biochemical and morphological properties of tissue. The physiological noise can be one of the most challenging to address. To alleviate this noise source is to normalize or compare the intensities measured at any tissue site with the intensity from a 'clinically normal' site. The normal site is identified using simple tests such as the maximum or minimum intensity or intensity ratio.

The signal to noise ratio of a measuring device is simply $$SNR = \frac{I}{\sigma(I)}$$

where I is the measured signal intensity, and $\sigma(I)$ is the noise or standard deviation of the measured intensity. We have taken steps to ensure that signal corruption in our device from the cumulative effects of these noise sources is reduced or eliminated. The specific steps include:

A. Obtaining a high enough signal intensity such that the noise in the measurement in dominated by the shot noise. The shot noise is an inherent property of the CCD response and given that it increases as $\sqrt{I}$ with increase in I, its proportion as a percentage of I decreases with increase in I. At a high value of I the contribution of shot noise is negligible. We have attempted, as listed below, to reduce other noise sources to a value below that of shot noise i.e. the instrument operates in the shot noise dominated regime;

B. Keeping the temperature and the A/D transfer rate at the lowest optimum, thus minimizing read and dark noise;

C. Measuring the lamp power simultaneously with the tissue measurement. The tissue measurement is then normalized by this measured lamp intensity. This removes/corrects for the noise in the measured intensity due to variability in lamp intensity and variability in the transmittance of optical components such as fibers, filters and lenses;

D. Using ratios of intensities at different wavelengths rather than straight intensities since this method internally corrects for changes in transmittance and also corrects for variations in light coupling due to changes in the way the target tissue is oriented with respect to the light beam. This method is limited to transmittance changes that do not vary across the spectrum; and E. Optimizing the clinical procedure to minimize the clinical noise. This includes an adequate tissue cleaning procedure and keeping the device weight and shape conducive to holding it without significant motion artifact.

Next, the horizontal dimension of the CCD, measured in pixel number is used to mark the wavelength of the measured intensity. A wavelength number is assigned to each pixel. Establishing these absolute scales contribute to the calibration of the present invention.

Calibration standards may include those commonly used by ones skilled in the art. For example, spectral irradiance standards may utilize a NIST traceable Quartz Tungsten halogen lamp for wavelengths greater than approximately 400 nm. For wavelengths less than approximately 400 nm, a NIST traceable Deuterium lamp may be used. Wavelength calibration standards may include, without limitation, mercury lamps and NRCC traceable Erbium Oxide lamps. With respect to the former, these lamps have narrow, discrete spectral lines over UV and visible wavelengths that provide a metric for wavelength calibration. For example, for diffuse reflectance standards, a NIST traceable Spectralon™ from LabSphere, Inc. (North Sutton, N.H.) may be utilized. The reflectance of these standards is highly lambertian over their spectral range. They also have a spectrally flat reflectance profile, i.e. the percent of radiation reflected at each wavelength (within the usable wavelength range) is constant. For diffuse fluorescence standards, ones such as those produced by LabSphere, Inc. may be used. These standards are also made of Spectralon™ and one further embedded with inorganic fluorophores that provide a highly stable, reproducible fluorescence.

In addition to absolute scale, calibration must correct for variances and potential external and/or internal interferences. Fluctuations in lamp intensity and spectral shifts may need to be corrected for, since arc lamps such as the ones used according to certain embodiments of the present invention are known to display fluctuations in energy output based on lamp life, duration of use and ambient conditions. Since the present invention determines tissue characteristics based on intensity measurements, such variations should be taken into consideration and accounted for by appropriate calibration. Similarly, it is helpful to correct for stray light that may result from the inability of a monochromator grating to perfectly separate light of different wavelengths. Grating efficiency, inadequate baffling and the use of short optical path lengths needed to make a compact instrument all contribute to stray light and therefore, should also be accounted for by appropriate calibration. In addition to stray light, background light may also be a factor to consider. Light leakage into the system that results in erroneously higher intensities must be measured and subtracted.

Finally, in addition to absolute scales and internal and/or external light factors, calibration of the present invention may also include accounting for dark noise and variance and temporal changes in optical properties, spectral transmittance, reflectance of lenses and fibers. With respect to dark noise, this issue primarily arises as a result of thermal, non-thermal and readout noise characteristics of the CCD detector. Although embodiments of the invention use a PET cooled detector, the noise can be significant and needs to be subtracted out. With respect to factors effecting optical properties, spectral transmittance, reflectance of lenses and fibers, each spot/location of light projected on the tissue varies in intensity. This variance may be due to the axial position of the spot and small differences in individual fibers and mask apertures. The intensities of the spots/locations may change with time due to changes in alignment and component degradation.

The present invention utilizes at least one calibration during its operation. One type of calibration is before the initial operation of a device embodying the invention or when the device needs maintenance and/or repair. This will be referred to as pre-operative calibration. Pre-operative calibration may comprise an absolute calibration protocol and a wavelength protocol.

Figure 21:
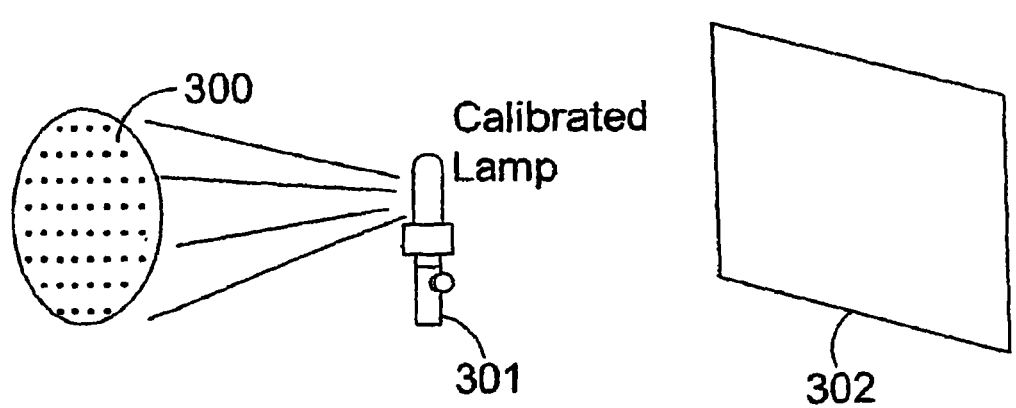
FIG. 21 is a schematic drawing of a setup for absolute calibration of a system embodying the invention.

Absolute calibration applies irradiance standards to establish performance benchmarks and to provide an absolute scale to the intensities measured. The irradiance standards allow the coupling of known intensity levels into fibers or apertures. A schematic diagram of a setup for performing calibration is shown in FIG. 21, where 300 designates an aperture mask, 301 designates a light source, and 302 designates a black absorbing material. The aperture mask 300 shown may be replaced with an excitation fiber bundle, where the light is coupled into fibers at one end of the bundle. The light emerging from the other side of these apertures or the other end of the fiber bundle can be imaged by the detection system and the measured intensity calibrated against the known intensity to arrive at a correction factor which will be further taught below.

To calibrate wavelengths, wavelength calibrations are used. The light source 301, such as a calibrated mercury arc lamp, is positioned between a focusing lens (not shown) and the mask 300 in FIG. 21 while the arc lamp is off or the safety shutter is closed to ensure only illumination from the mercury lamp enters the system. A reflectance target is held before the sight tube, taking care to seal off and prevent room light from entering the system. The columns of illuminated spots are spectrally resolved on the CCD. The known natural peaks of the mercury spectrum, when the embodiment is a mercury lamp, are captured and are used for calculating a wavelength scale for each image. A set of eight software driven measurements that account for each of the eight column positions on the target, are made as show in the table of FIG. 22 using the instrument settings indicated for each measurement.

In addition to, or alternatively, the present invention can be calibrated prior to each measurement. This calibration will be referred to as "operative calibration". This calibration corrects for both short-term system, intermediate and long-term fluctuations, such as lamp degradation, for example. The method that performs this calibration may be embodied in a software program using the instrument settings listed in the tables of FIGS. 23 and 24.

The operative calibration comprises a reflectance calibration, a fluorescence calibration, and a background and dark noise calibration. The reflectance calibration may, according to certain embodiments, comprise of positioning the Spectralon™ diffuse reflectance target before the sight tube so as to exclude room light from the system. A series of measurements given the instrument settings listed in the table of FIG. 23 are made. During a fluorescence calibration, the Spectralon™ (or other comparable) fluorescence target is positioned before the sight tube taking care to exclude room light or other superfluous light from the system. A series of measurements given the instrument settings listed in the table of FIG. 24 are made according to one embodiment of the present invention. According to this embodiment, the measurements may be made in sets of three where each set may use a different excitation and emission wavelength selected by choosing a different filter set.

Finally, background and dark noise calibration may be incorporated into the fluorescence and reflectance and calibrations above as well as into each subject target tissue/area measurement. According to certain embodiments, the first measurement of each sequence of 8+1 measurements in the tables of FIGS. 23 and 24 is a background measurement where the safety shutter is held closed. This measurement accounts for the error that may be caused due to room light and/or other electronic noise sources that may result in the CCD reading an intensity signal. This type of result may be defined as background noise and is subtracted from each of the calibration and tissue measurements.

The data collected from pre-operative and/or operative calibrations are used to calculate a set of correction factors for absolute calibration as follows:

$$C(f, \lambda) = T(f, \lambda)/M(f, \lambda)$$

where f is the position/spot number or aperture location in the target area and $\lambda$ is the wavelength (~400-700 nm). $T(f, \lambda)$ is the true intensity from the standard coupled into the aperture at least one wavelength, and $M(f,\lambda)$ is the intensity measured by the system from that aperture at that at least one wavelength. All spectra acquired with the same detection system can then be multiplied point-for-point by these correction factors in order to eliminate effects of the non-uniform response (spectral and spatial) of the detection system.

In calibrating wavelengths, the measured spectrum of a mercury light source contains sharp peaks which correspond to the spectral lines of the source. The wavelength of each corresponding spectral line can be assigned to the pixel number along the horizontal axis of the CCD for each position of the peak. With two or more peaks present in the spectrum, a linear interpolation is then used to determine the wavelength values for all the pixels.

For operative calibration, the protocol comprises a reflectance intensity calibration, a fluorescence intensity calibration, and a stray light or other superfluous light calibration. Intensity calibration measurements for reflectance spectra are performed by normalizing the spectrum measured from each spot on a tissue with the spectrum measured from the same spot on the reflectance calibration target. This is done after subtracting the background light from each measurement. This procedure eliminates any error from spot-to-spot variations in excitation intensity and can be expressed as follows:

$$R(f, \lambda) = \{[RS(f, \lambda) - BS(f,\lambda)]/[-RR(f,\lambda) - BR(f,\lambda)]\} = TR(f, \lambda),$$

where $RS(f,\lambda)$ is the reflected intensity spectrum measured from the subject target area and $RR(f, \lambda)$ is the reflected intensity spectrum measured from a reference whose true reflectance $TR(f, \lambda)$ is known. This true reflectance is provided by a diffuse reflectance standard whose reflectance is substantially constant for all wavelengths used in the system taught by the present invention.

$BS(f, \lambda)$ is the background measurement corresponding to the tissue reflectance measurement, e.g. tissue background measurement taken using the same instrument settings as the tissue measurement, but with the safety shutter closed. $BR(f,\lambda)$ is the background measurement corresponding to the reference measurement. With these measurements, a meaningful estimate of tissue reflectance $R(f, \lambda)$ may be obtained.

For fluorescence spectra, intensity calibration involves normalizing the fluorescence spectrum from each location on the target area by the fluorescence intensity from the same location when measuring on the fluorescence calibration target. Then, either the integral or the peak of each position's intensity spectrum may be used to normalize spectrum using the following formula:

$$F(f, \lambda) = [FS(f, \lambda) - BS(f,\lambda)]/[FR(f,v.) - BR(f, \lambda)]$$

where $FS(f, \lambda)$ is the fluorescence spectrum measured on subject target area and $BS(f, \lambda)$ is the corresponding background measurement taken using the same instrument settings as the subject target area measurement but with the safety shutter closed, $FR(f, \lambda)$ is the measurement on the fluorescence reflectance standard, $BR(f, \lambda)$ is the corresponding background measurement, and $F(f, \lambda)$ is the corrected fluorescence spectrum.

With respect to stray light or superfluous light calibration, correcting each fluorescence spectrum for the stray light output of the excitation monochromator involves subtracting the stray light spectrum reflected from the tissue from the measured fluorescence spectrum of the tissue. This correction employs the principle that the absolute reflectance (as a function of wavelength) is independent of the spectrum used for illumination. This principle can be expressed as an extension of the immediately preceding equation as follows:

$$\{RS[I_1(f, \lambda)] - BS[I_1(f, \lambda)]\}/\{RR[I_1(f,\lambda)] - BR[I_1(f, \lambda)]\} =$$

$$\{R_S[I_2(f, \lambda)]\}/\{RR[I_2(f,\lambda)] - B_R[I_2(f, \lambda)]\}.$$

Here, $I_1$ is the standard, broadband output of the illumination system used to measure reflectance of tissue, for example, and $I_2$ is the stray/superfluous light of the illumination system that accompanies the monochromatic excitation used for tissue fluorescence measurements. Thus, tissue calibration may be achieved by normalizing this procedure with the standard reflectance. The result is a calibration factor, as follows:

$$\{RS[I_1(f, \lambda)] - BS[I_1(f,\lambda)]\}/\{RR[I_1(f,\lambda)] - BR[I_1(f,\lambda)]\}$$

which when multiplied by the stray/superfluous light spectrum measured on the standard from supposedly monochromatic excitation gives the stray/superfluous light inadvertently measured along with tissue fluorescence. This is illustrated by rearranging the equation such that:

$$RS[I_1(f, \lambda)] = (\{RS[I_1(f, \lambda) - BS[I_1(f, \lambda)]]\}/\{RR[I_1(f, \lambda.) - BR[I_2(f, \lambda)]]\}) =$$

$$\{RR[I_2(f, \lambda)] - BR[I_2(f, \lambda)]\}.$$

$RR[I_2(f,\lambda)]$ and the corresponding $BR[I_2(f,\lambda)]$ are measured in a similar way as discussed in the previous section for intensity calibration of fluorescence spectra. The reflectance standard is illuminated with monochromatic light (and associated stray light), and the measurement focuses on wavelengths at which stray light is present (i.e. longer than the excitation wavelength) rather than the excitation bandwidth. $RR[I_2(f,\lambda)]$ is then subtracted from the measured fluorescence spectrum.

After the present invention has been calibrated, the tube 72 of the tissue interface unit 70 may be first inserted into the patient's vagina so that the end of the tube is immediately adjacent, or covering the patient's cervix. The cervix is then illuminated by the illumination source 76. Collected optical energy transmitted and/or reflected from the tissue is directed to the imaging device 78, which, in this embodiment, is located in the tissue interface unit 70. The imaging device 78 sends a video signal that is viewed with a computer or video monitor (not shown). Thus, the imaging device 78 provides the user with a view of the patient's cervix, which assists the physician in properly aligning and situating the tube 72 with respect to the patient's cervix. The imaging device 78 may also be used to capture still images of the cervix, which may be digitally stored and used for later data analysis.

The tube 72 is appropriately placed such that a good view of the subject target area can be seen through the imaging device 78, the tissue interface unit is fixed in place relative to the subject target area. At this point, a still picture of the subject target area may be taken with the imaging device. The illumination device 76 is then turned off, and the spectroscopic measurements are started. As described above, a series of measurement cycles would be conducted. During each measurement cycle, a column of positions on the subject target area would be illuminated, and the light returning from the subject target area would be detected by the detection sub-unit. During each measurement cycle, the spectrograph would spectrally resolve the column of positions into a two-dimensional image that is captured by the camera 58. Each two dimensional image would be arranged such that one axis is indicative tissue position, and the other perpendicular axis would be indicative of wavelength. The two dimensional images recorded during the measurement cycles would then be recorded and analyzed by the device operating software in the control sub-unit 45.

Figure 7A:
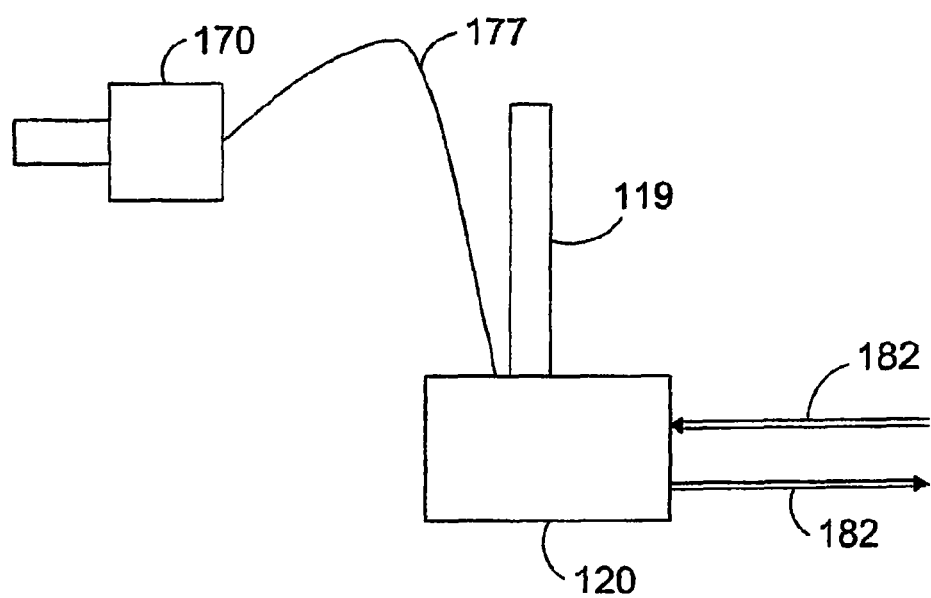
FIGS. 7A and 7B are schematic drawings of a system for determining tissue characteristics according to another embodiment of the invention.
Figure 7B:
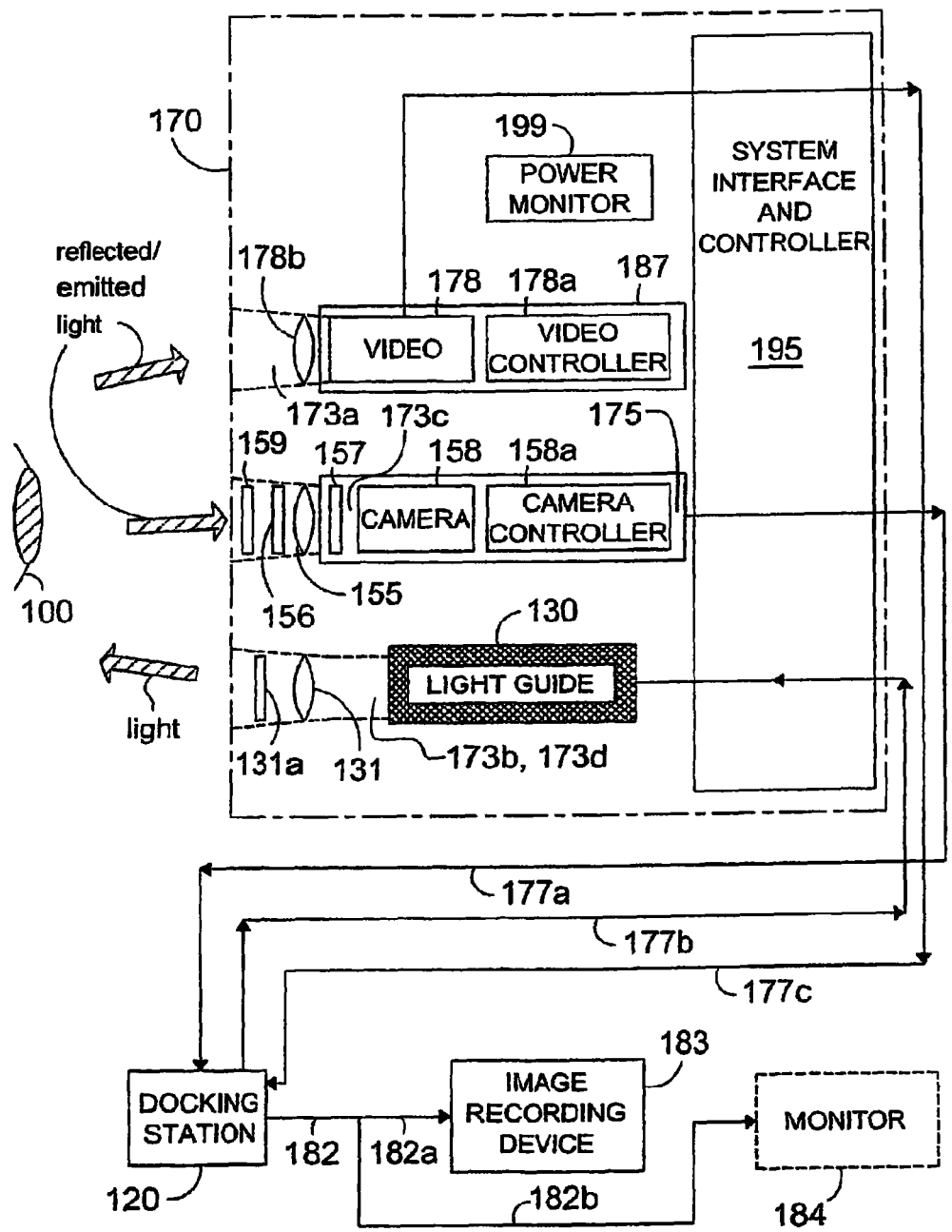

FIGS. 7A and 7B are schematic drawings of a system for determining tissue characteristics according to another embodiment of the invention. The system 110 includes a tissue interface unit 170, which may be configured as a handheld probe-type unit, and a docking unit 120. The tissue interface unit 170 and the docking unit 120 communicate with each other via communication pathway 177, which may comprise one or more optical fibers or other type of signal cable.

The docking unit 120 may include a stand or cradle 119 for docking or holding the tissue interface unit 170 when not in use. The docking unit 120 may also include one or more pathways 182 for outputting or receiving signals to or from additional system components, such as a image recording device, such as a VCR or other type image recording device 183 or monitor 184, such as a color TV monitor (shown in FIG. 7B).

As shown in FIG. 5A, the docking unit 120 may further include a processor 190, a power supply 191, an illumination source 132 and an illumination source controller 132a. The docking unit 120 may also include a light guide (not shown), such as a liquid light guide that guides optical energy from the illumination source, for example, into an optical fiber or other type cable to be delivered to the tissue interface unit 170.

As shown in FIG. 7B, the tissue interface unit 170 includes illumination pathways 173b, 173d, which may comprise a single or multiple pathways. These pathways 173b, 173d may include one or more light guides 130 that receive optical energy from the illumination source 132 disposed in the docking unit via communication pathway 177b. The tissue interface unit may also include an illumination lens assembly 131 and an illumination aperture/filter 131a that provides for selective wavelength filtering and a shutter function, also shown in FIG. 7B.

The tissue interface unit 170 further includes a collection pathway 173c, which guides optical energy reflected and/or emitted by a subject tissue to a device for making spectroscopic measurements 175. The device for making spectroscopic measurements 175 may include a diffraction grating 157, a camera 158, and camera controller 158a. The camera and camera controller may be, for example, a CCD camera controlled by a CCD camera circuit card assembly. The spectroscopic measurements may be sent to the processor 190 disposed within the docking unit 120 via communication pathway 177a for processing. According to one embodiment of the invention, the system is capable of detecting reflectance information between approximately 360 nm and 660 nm at a resolution and fluorescence information at 2 or 3 wavelength bands. According to various embodiments, the resolution and wavelength bands can range from 2 nm to 30 nm. According to one embodiment, the resolution is at 20 nm as are the wavelength bands. Each frame of data is transferred from the tissue interface unit to the docking unit for processing.

The collection pathway 173c may include a shutter 156 that blocks out illumination optical energy when spectroscopic measurements are not being made, a filter 159 that provides for selective filtering of wavelengths not of interest, and a collection lens assembly 155.

The tissue interface unit 170 may further include an imaging pathway 173a that guides reflected optical energy to an imaging device 187. The image pathway 173a may also include a lens assembly 178b. The imaging device 187 comprises, for example, camera 178 and camera controller 178a. The camera and camera controller may be, for example, a video camera and video camera controller, or any similar type image recording device. The video imaging channel according to one embodiment may have a resolution of 300 TV lines (NTSC analog output for video recording and display) with fixed magnification and focus, a field of view of approximately 25 mm, and a depth of field of approximately +/−5 mm. The imaging device 187 allows a user to view the subject tissue in order to position the tissue interface unit 170 with respect to the subject tissue. The tissue interface unit 170 may include a monitor, or may communicate with a separate monitoring device to permit viewing of the tissue by a user. Additionally, the tissue interface unit 170 may include a user interface (not shown) that provides for entry of patient information, for example.

Figure 8A:
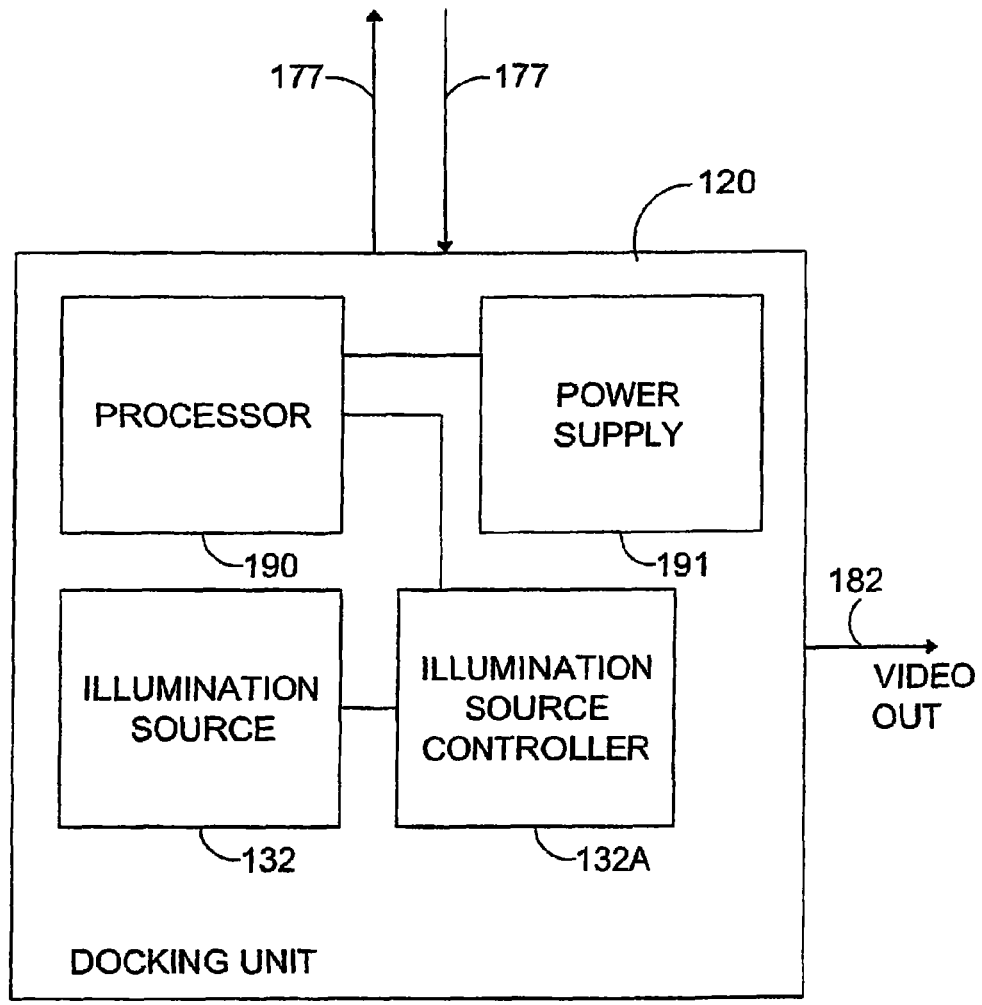
FIG. 8A is a schematic drawing of a docking unit of a system for determining tissue characteristics according to another embodiment of the invention.
Figure 8B:
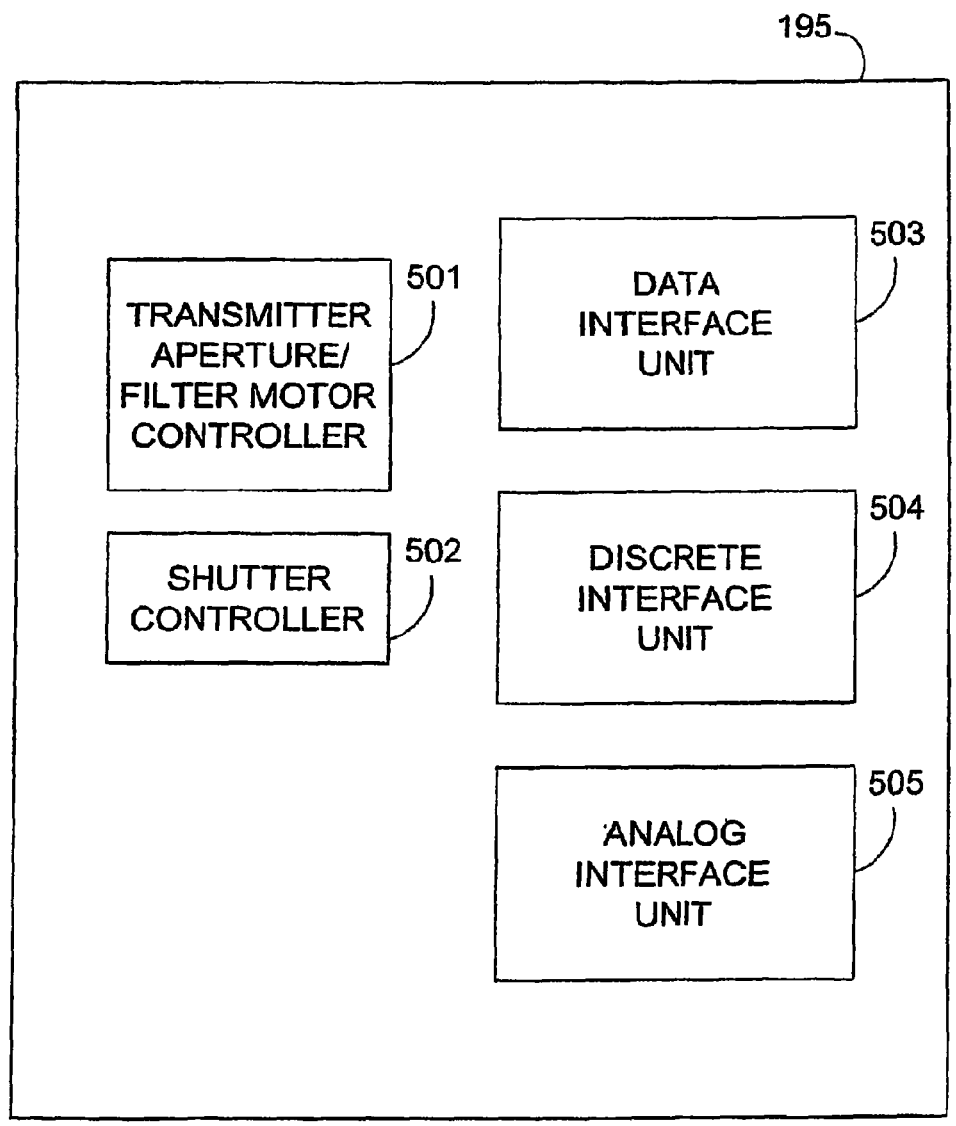
FIG. 8B is a schematic drawing of a system interface and controller of a system for determining tissue characteristics according to another embodiment of the invention.

The tissue interface unit further includes a power monitor 199 and a system interface and controller 195, as shown in FIG. 7B. As shown in FIG. 8B, according to one embodiment of the invention, the system interface and controller 195 includes a data interface unit 503 that controls the exchange of data signals between the tissue interface unit 170 and the docking unit 120. The system interface and controller 195 may further include a discrete interface unit 504 that controls the system's respective power and switches, and an analog interface unit 505 that controls the systems interface with an external image recording device 183. The system interface and controller 195 may also include a shutter controller 502 that controls operation of shutter 159 and an illumination aperture/filter controller 501 that controls operation of the motor of the illumination filter.

Figure 11:
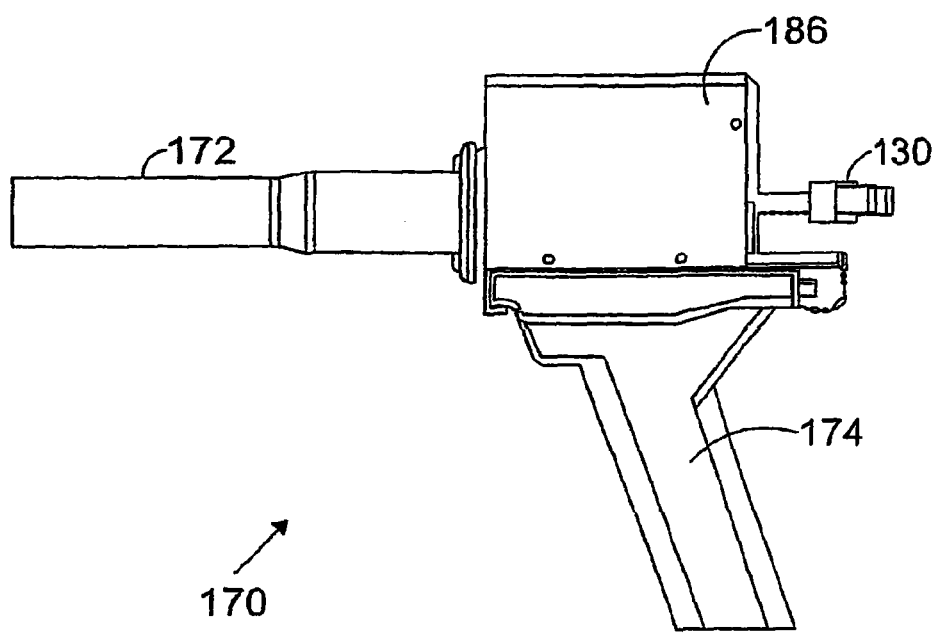
FIG. 11 is a side view of a tissue interface unit of a system for determining tissue characteristics according to another embodiment of the invention.
Figure 12:
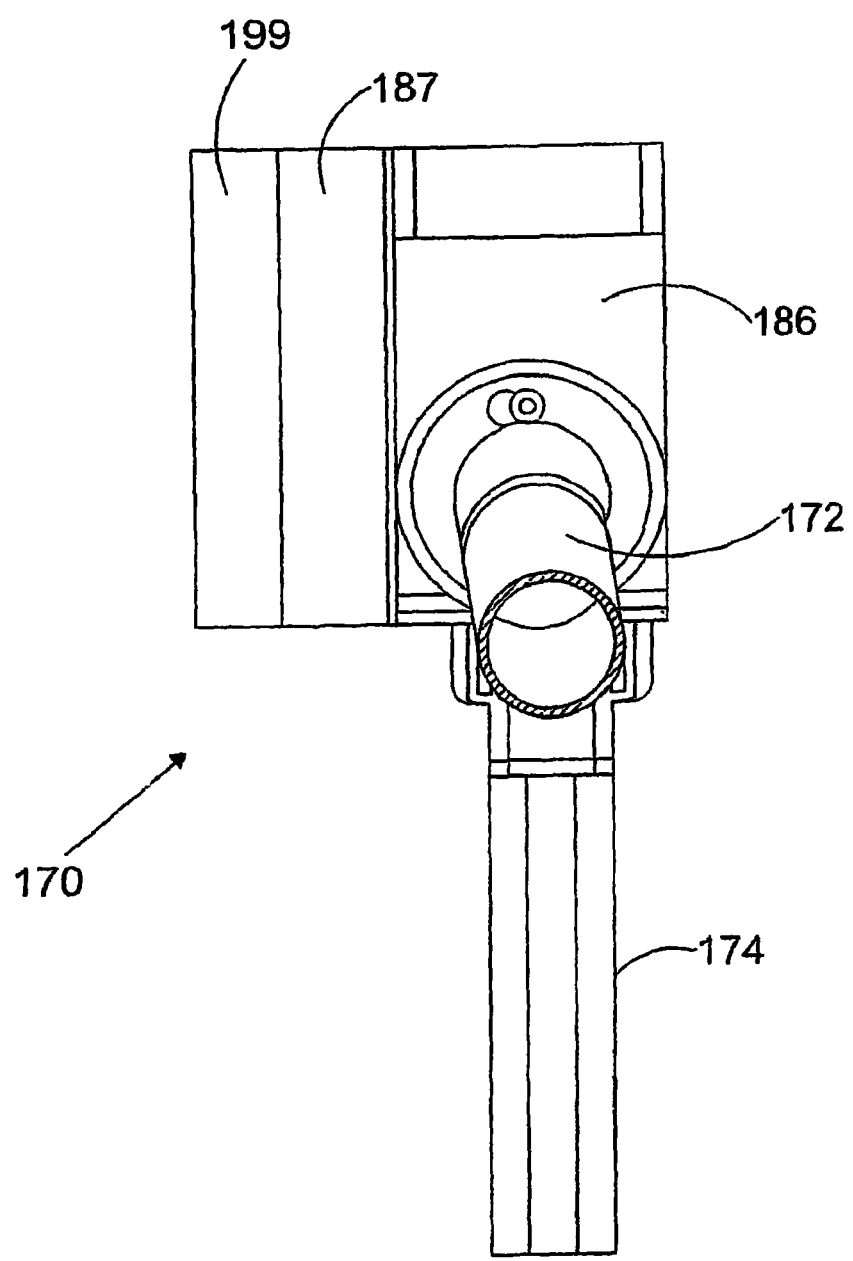
FIG. 12 is a front perspective view of a tissue interface unit of a system for determining tissue characteristics according to another embodiment of the invention.

An example of one embodiment of a hand-held tissue interface unit according to the invention is shown in side view in FIG. 11. The tissue interface unit 170 includes housing 186, a handle 174 configured to be graspable by a user, a tube 172 that delivers illumination optical energy to a subject tissue, and optical energy reflected and/or emitted by the subject tissue to the viewing device and/or the spectroscopic measurement device, and a liquid light guide 130 that guides optical energy received from a docking unit 120 into the tube 172. The tube 172 may be removable, as discussed below, and may be disposable. As shown in FIG. 12, the tissue interface unit 170 may also include a heat sink 199 that maintains the tissue interface unit within an acceptable temperature range.

Figure 9:
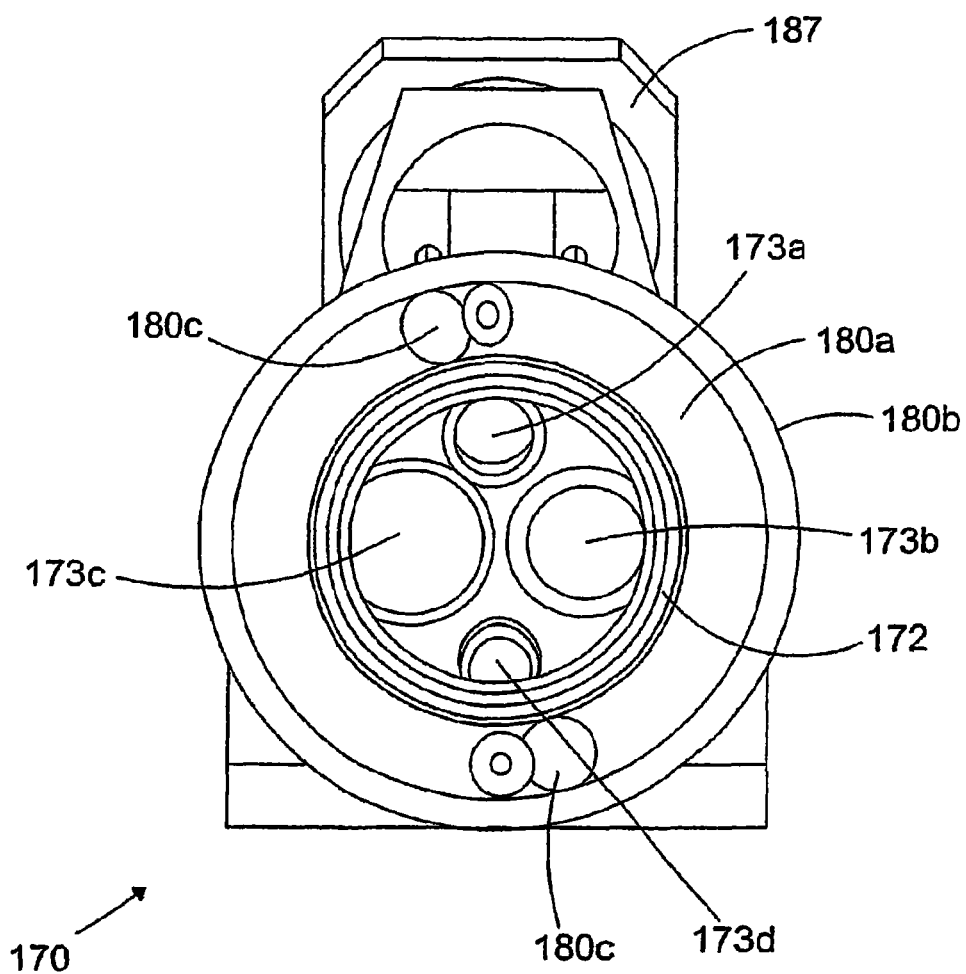
FIG. 9 is a front view of a tissue interface unit of a system for determining tissue characteristics according to another embodiment of the invention.
Figure 10:
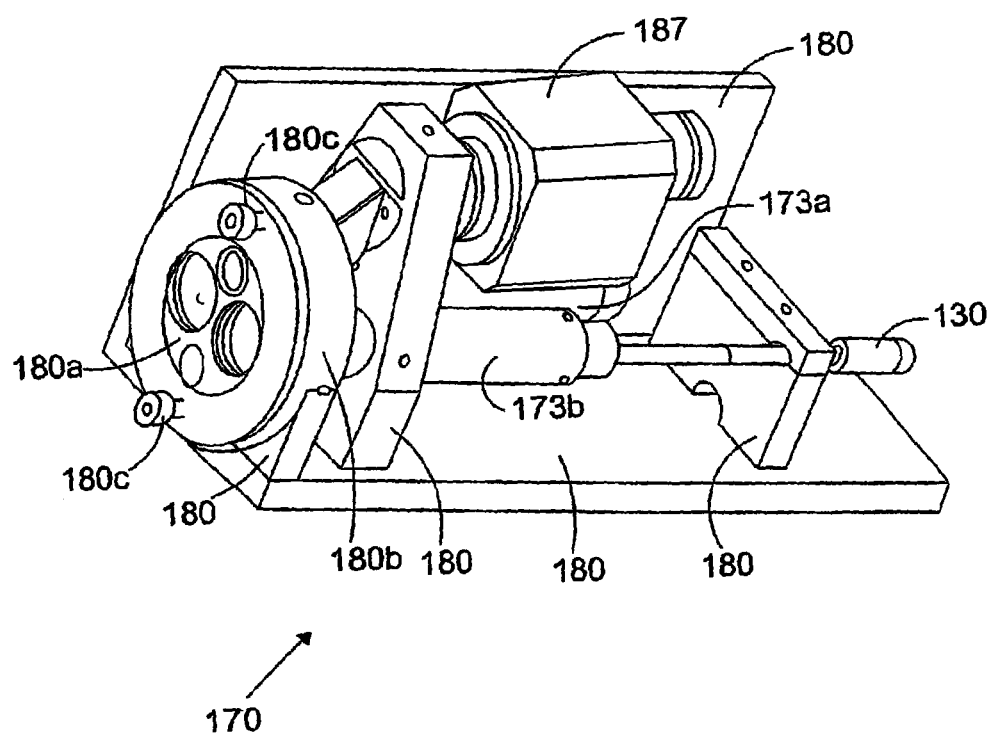
FIG. 10 is a side perspective view of the tissue interface unit of a system for determining tissue characteristics according to another embodiment of the invention.

FIG. 9 is a front view of a tissue interface unit according to the invention without outer casing 186, and handle 174. FIG. 10 is a side perspective view of the tissue interface unit of FIG. 9 without outer casing 186 and tube 172. As shown in FIGS. 9 and 10, the tube 172 connects to the base structure 180 via a plate 180b. The plate 180b has an endface 180a. The endface 180a includes openings for illumination pathways 173b, 173d, collection pathway 173c and imaging pathway 173a. These pathways share tube 172 in such a way that no interference occurs between pathways. Tube 172 may be attached to endface 180a by some type of attachment means 180c, as shown in FIG. 9.

In an embodiment of the invention configured to detect tissue characteristics of a patient's cervix, the tube 172 of the tissue interface unit 170 may be first inserted into the patient's vagina so that the end of the tube is immediately adjacent, circumscribing or covering the patient's cervix. The cervix is then illuminated by the illumination source 132 via illumination pathway 173d. Collected optical energy transmitted and/or reflected from the tissue is directed to the imaging device 187, which is located in the tissue interface unit 170. The imaging device 187 sends a video signal that is viewed with a computer or video monitor. Thus, the imaging device 187 provides the user with a view of the patient's cervix, which assists the physician in properly aligning and situating the tube 172 with respect to the patient's cervix. The imaging device 187 may also be used to capture still images of the cervix, which may be digitally stored and used for later data analysis.

Once the tube 172 is appropriately placed such that a good view of the cervix can be seen through the imaging device 187, the tissue interface unit would be fixed with respect to the patient's cervix. At this point, a still picture of the cervix may be taken with the imaging device. The image signal is output to the docking unit or directly to a monitor provided within the tissue interface unit, or as a separate component. For example, the image, along with relevant text, could be displayed on a hand-held LCD unit or a LCD unit attached to the tissue interface unit. The spectroscopic measurements are then started. The spectroscopic measurement results are sent to the processor 190 in the docking unit 120 for processing. For example, the results can be utilized to categorize the spectroscopic measurement data, and thus the subject tissue, as "Normal", "Non-Dysplastic", "Low Grade SIL", and "High Grade SIL."

The systems, methods and apparatus of the present invention, may conduct both fluorescence and reflectance spectroscopy using both visible and UV light or any combination thereof. This is generally referred to as multimodal spectroscopy. Cervical cancer, being a form of epithelial dysplasia, provides an ideal target for diagnosis using the epithelium down to the germinative layer, since it undergoes minimum absorption and scattering from non-specific interactions and obtains the largest possible diagnostic information on its biochemical and morphological state. Other areas with similar qualities that may serve as comparable targets for diagnosis include, without limitation, oral cancer and colon cancer.

Fluorescence and reflectance spectra may be made at several locations on the target area by the present invention. Such locations may be equispaced. Obtaining measurements across the entire target area, for example, may allow for differential diagnosis between dysplasia and surrounding tissue depending on the embodiment.

Many investigators have pointed to the large biological variation in the spectroscopic signature of normal tissue. This natural variation is often higher than the variation seen in the spectroscopic signatures going from normal to dysplasia tissue in the same patient, for example. One cannot, therefore, assign an absolute spectral intensity or signature to disease state. Rather, all measurements must be normalized or baselined to "normal" tissue in the same patient, and it is this relative measure or change that has diagnostic relevance. Given our inability to determine "a priori" the location of abnormal and normal tissue with certainty, the logical alternative is to measure substantially the entire target area.

A reflectance measurement is made by measuring the intensity of light returned from the tissue at the same wavelength as that used to irradiate the tissue. Reflectance measures the morphological changes associated with dysplasia progression. Although biochemical changes precede the morphological changes that occur as a result of the former, in reality, varying degrees of morphological change accompany the biochemical changes. Morphological changes appear later in the course of dysplasia progression and are defined as any change in average cell nuclei, cell size, cell appearance, cell arrangement, and the presence of non-native cells. In addition, effects of the host response such as increased perfusion from angiogenesis result in an overall difference in tissue appearance.

The morphological changes add more complexity to the fluorescence measurement by absorbing and scattering both the excitation and fluorescent light, thereby altering the true fluorescence signal. Thus, it is difficult to make a fluorescence measurement that is truly independent of the effects of scattering and absorption. At the same time, both measurements provide information that is partially independent of one another.

In reflectance spectroscopy, the tissue properties of absorption and scattering dictate the amount of radiation measured at the detector. For example, the increased vascularization due to angiogenesis causes increased blood absorption of visible light. Light propagating through and re-emitted from tissue is also strongly affected by light scattering interactions. For example, dysplasia cells have enlarged nuclei and since nuclei have a different refractive index from that of the cell cytoplasm, they serve as efficient light scatters. Thus, dysplasia tissue can display increased light scattering.

While the absorption and scattering properties of tissue correlate quantitatively with disease, by knowing the absorption and scattering at each site on the tissue the corresponding error that these effects produce in the fluorescence yields can also be corrected for. This is the crux of the multimodal spectroscopy approach. In order to reap this advantage, both measurements must be made on the same site at the same time so as to ensure nearly identical conditions.

The use of near LTV and UV wavelengths elicits the fluorescence and reflectance response of intrinsic markers shown to be highly indicative of biological and morphological changes caused by pre-dysplastic conditions in tissue. Accordingly, the systems, methods and apparatus according to the invention may be configured to acquire broad absorption and fluorescent spectra (approximately 340 nm to 700 nm). Particular examples of illumination and collection wavelengths are shown in FIG. 6. Although these wavelengths have shown promise, the invention is in no way limited to the use of these wavelengths.

The measurements are made from a predetermined standoff distance from the tissue. In one embodiment constructed by the inventors to detect abnormalities on cervical tissue, the standoff distance was set to approximately 175 mm (17.5 cm) to the first optical surface of the tissue. This standoff distance can be defined by and maintained by the length of the tube 72, 172 on the tissue interface unit 70, 170.

In order to capture high-resolution spectral data from several locations in a short time (hyperspectral imaging) design compromises are required. By compromising on the spatial resolution and measurement time, fluorescence and reflectance spectra can be captured at approximately 10 nm spectral resolution according to certain embodiments.

In one embodiment of the invention used to take measurements on a subject tissue, for example, a cervix, the system uses a line-scan approach to collect data from a plurality of detection points. After positioning, measurements are made at, for example, 52, approximately 0.5-mm circular spots nominally separated from each other by approximately 3.0 mm, as shown in FIG. 5. The subject tissue is first flooded with illumination optical energy. Optical energy returned by the subject tissue is fed to a viewing device, which provides a user with an image of the tissue so that the user can appropriately position the system with respect to the subject tissue. Next, a single line or column of points on the tissue is illuminated with optical energy. According to one embodiment, the optical energy is illuminated in a range of approximately 340-700 nm. The radiation/light returned from the target tissue is collected using a coherent fiber bundle. The result is that the collected optical energy is formed into a virtual slit at the entrance of the spectrograph. The spectrograph is then used to spectrally resolve the optical energy. Given the spectral resolution required, and the dispersion by the spectrograph, in this embodiment, a single column is measured at any given time. The system sequentially scans through all eight columns shown in FIG. 5, acquiring both fluorescence and reflectance spectra in a total time duration of approximately 2 minutes.

According to another embodiment of the invention, the system uses a flood illumination approach. The subject tissue is first flooded with illumination optical energy. Optical energy returned by the subject tissue is fed to a viewing device, which provides a user with an image of the tissue so that the user can appropriately position the system with respect to the subject tissue. After positioning, the subject tissue is again flooded with illumination optical energy, for example, in a range of approximately 340-700 nm.

Figure 20A:
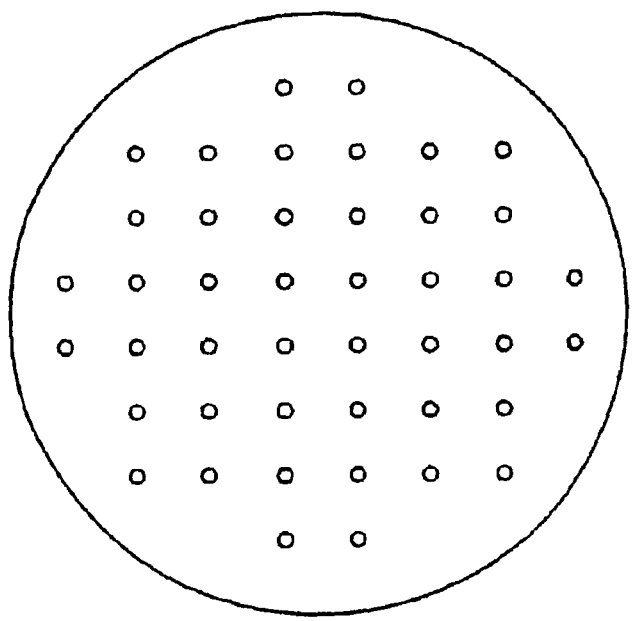
FIG. 20A is a schematic drawing of an illumination or target end of a fiber optic bundle.
Figure 20B:
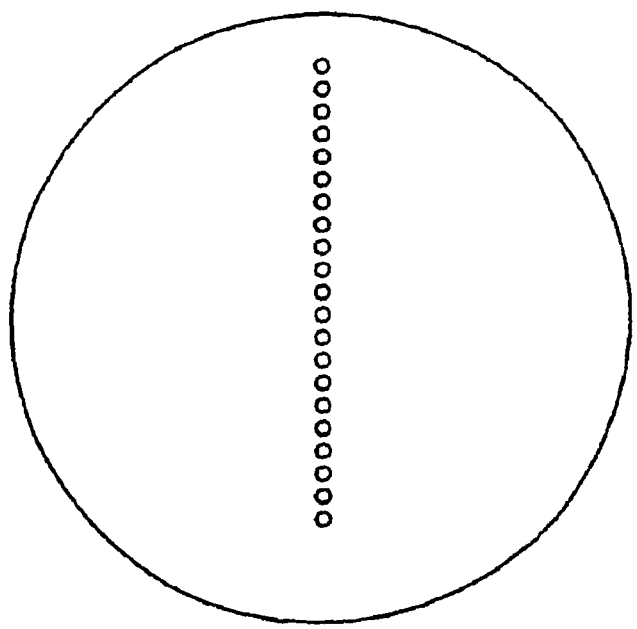
FIG. 20B is a schematic drawing of a collection end of the fiber optic bundle of FIG. 20A, illustrating a collection approach according to the invention.

The optical energy reflected and/or transmitted with respect to the subject target area is imaged with the help of a set of optics onto the face of a fiber bundle (target end) as shown in FIG. 20A. This end of the fiber bundle has fibers arranged at discrete points, as shown in FIG. 20A, and the light imaged onto the bundle at these points is transferred via the fibers to the other end of the bundle, as shown in FIG. 20B. The other end of the bundle has all of the fibers arranged in a single column. This column serves as the entrance slit of the spectrograph, which is then able to spectrally resolve, in the horizontal direction, the light in this column.

In another embodiment, the optical energy is directed to the subject target area with the help of a set of optics that images a mask of apertures onto the tissue. This is an alternative embodiment to those embodiments taught and described in FIGS. 4 and 5. The apertures are arranged in a column on the mask. The mask can be horizontally moved to scan the entire subject target area while presenting at least one single column of light at the entrance of the spectrograph at a given instant. The spectrograph is then able to spectrally resolve, in the horizontal direction according to an embodiment, the light collected by this column of apertures.

The optical energy reflected and/or transmitted by the subject tissue is then collected and directed to a diffraction grating, which separates the light spectrally. Wavelengths not of interest may be filtered out. For example, the illumination wavelength may be filtered out. The collected light is then reflected onto a device for making spectrographic measurements, such as a CCD camera and controller.

Figure 13:
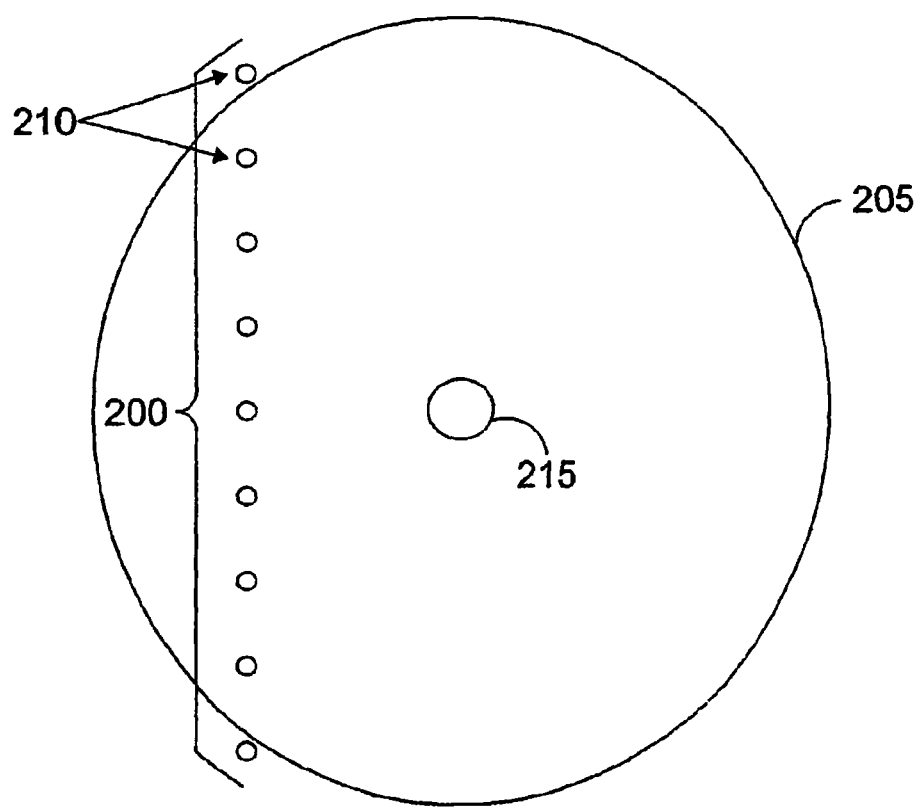
FIG. 13 is a schematic drawing showing an exemplary arrangement of detection points on a subject tissue.
Figure 14:
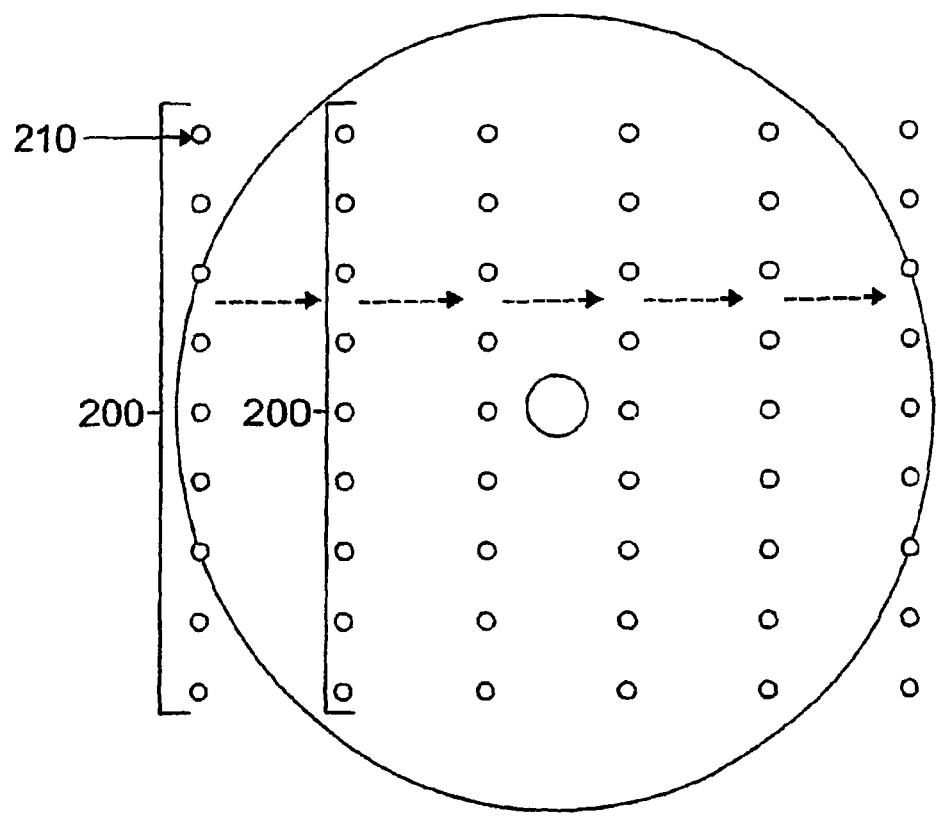
FIG. 14 is a drawing schematically showing how measurements of columns of detection points are sequentially taken across a subject tissue according to one embodiment of the invention.

As in the previous embodiments, the spectrograph only makes measurements at a single column 200 of detection points 210 at a time on a subject tissue 205, as shown in FIG. 13. According to an embodiment, reflectance measurements and fluorescence measurements are made at fifty-six points on the cervix with a separation of approximately 3 mm. However, depending on the embodiment, the number of points can vary to any number of possible points at a separation sufficient to avoid optical cross-talk/interference among the points. Reference numeral 215 represents a center of the subject tissue, in the case of a cervix this would be the Os. Measurements for various columns are then sequentially made, as shown in FIG. 14.

Figure 15:
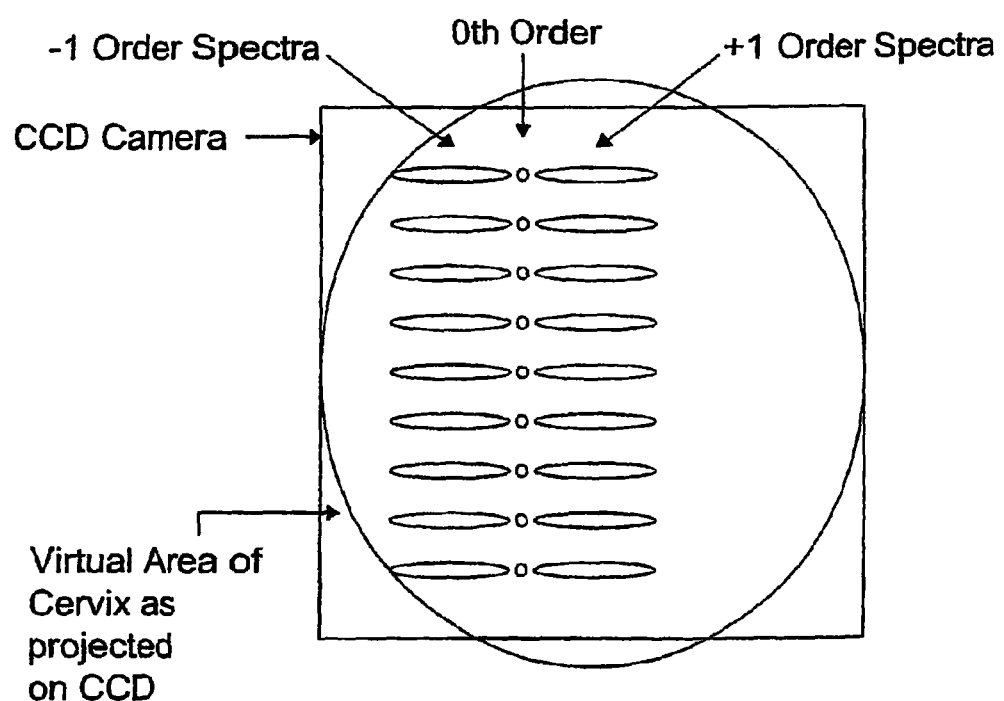
FIG. 15 is a drawing schematically showing an exemplary arrangement of a column of detection points on a CCD camera according to the invention.

FIG. 15 schematically shows what would be recorded by a CCD camera coupled to the output of a spectrograph. The light returning from a column of locations on the cervix would be spectrally resolved into different wavelengths that extend away from the column in a perpendicular direction. In other words, the pixels of the CCD camera extending to the left and the right of a single measurement position would received light of different wavelengths returned from the measurement position. The intensity of the light received at each pixel is indicative of the intensity at a particular range of wavelengths. Thus, examining the values registered at each pixel on the CCD array allows the device to determine the intensity of the light returned from each position on the illuminated column of positions at a plurality of different wavelengths.

Figure 16:
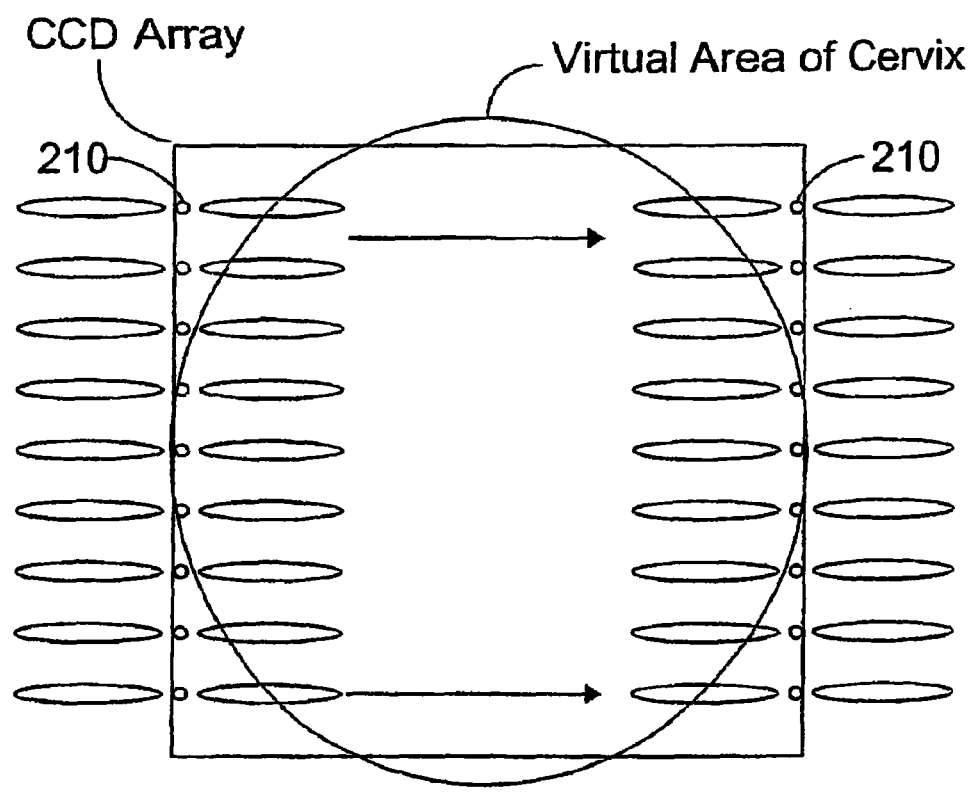
FIG. 16 is a drawing schematically showing the projection of an image across a CCD camera according to the invention.

FIG. 16 schematically shows how a series of measurements would be taken during different measurement cycles. Each measurement cycle would provide information about the light returned from a different column of illuminated positions on the target tissue.

Figure 17:
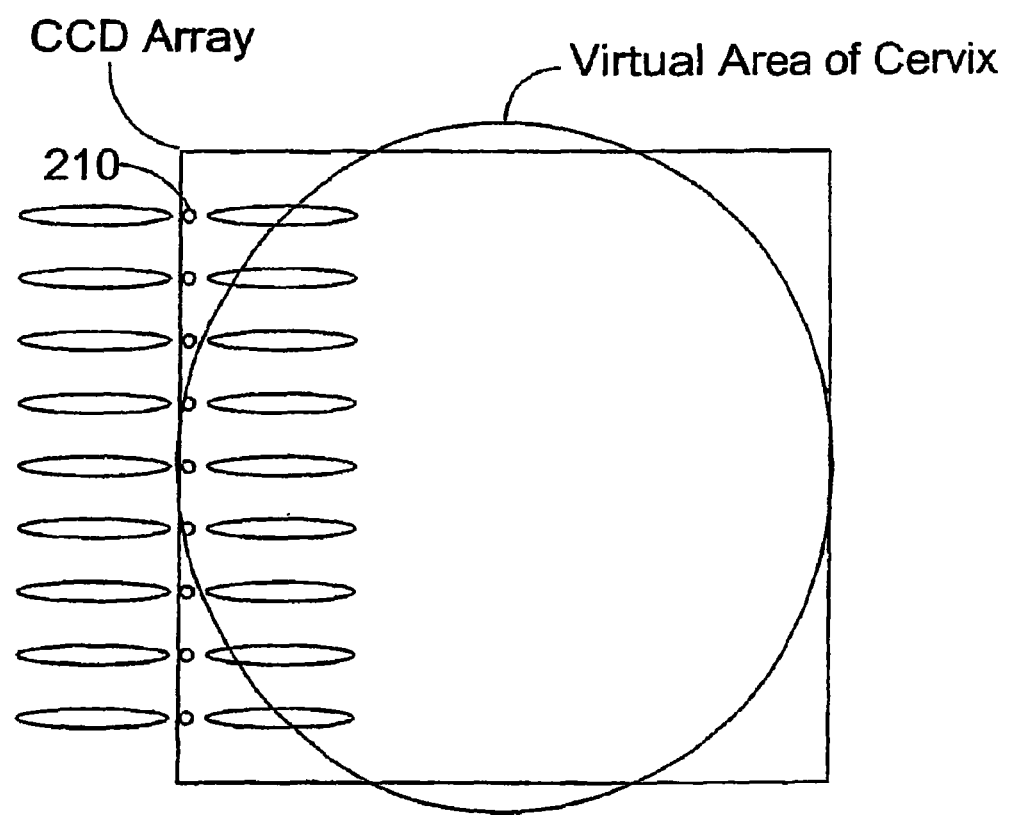
FIG. 17 is a drawing schematically showing an image of a left side of a cervix projected onto a CCD camera according to the invention.
Figure 18:
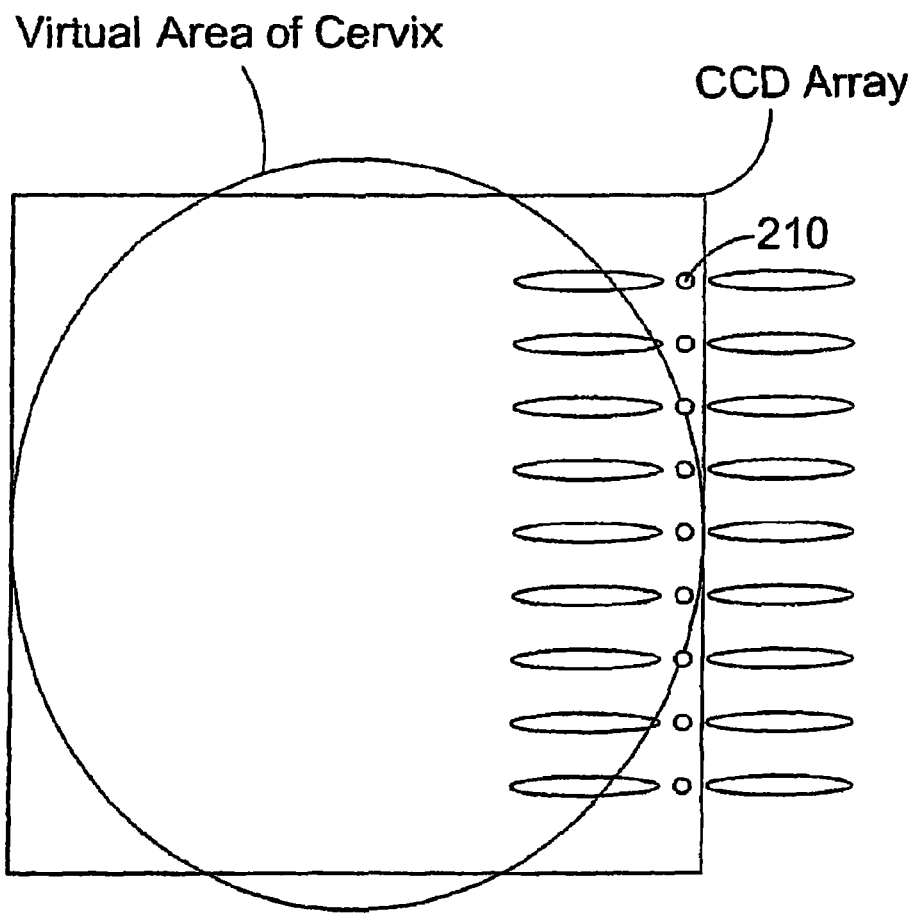
FIG. 18 is a drawing schematically showing an image of a right side of a cervix projected onto a CCD camera according to the invention.

Note, the spectrograph would separate the light from each illuminated measurement position 210 into a +1 Order Spectra and a −1 Order Spectra. Each Spectra would contain essentially the same spectral information. Thus, when interrogating a column of positions 210 on the left side of the cervix, as shown in FIG. 17, the device could utilize the +1 Order Spectra, which illuminates pixels within the CCD array. When interrogating a column of positions 210 on the right side of the cervix, as shown in FIG. 18, the device could utilize the −1 Order Spectra.

In cases where the entire spectral bandwidth is not available in either the +1 or the −1 order spectra, appropriate wavebands from both orders will be combined to form a complete spectral set.

Figure 19:
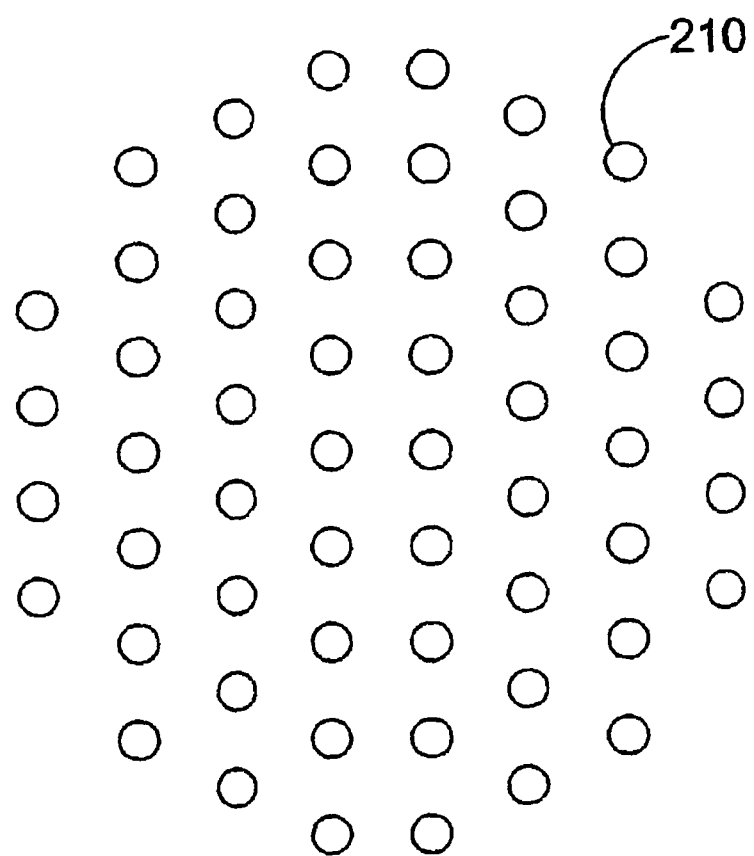
FIG. 19 is an exemplary arrangement of detection points for a cervix according to the invention.

FIG. 19 schematically shows the ultimate arrangement of detection points 210 collected for an entire cervix using this system.

In a further embodiment, an improved non-invasive device and method are disclosed. Some of the objectives may be:

1. The potential for a truly non-invasive test. Replacing physical biopsy and histology of tissue with "optical biopsy",
2. The potential for providing results at the point of care. The present invention does not require reading cytology or histology slides following sample collection from the patient. Since the tissue in the patient is interpreted using the present invention algorithm at the point of care, follow-up consultation with the test results in hand is made possible.
3. Improved detection and diagnosis. There is improved discrimination using fluorescence and reflectance spectroscopy.
4. The test can be performed by a 'non-specialist'. The performance of the present invention will be compared to colposcopy and biopsy/pathology. The present invention can remove or alleviate this 'subjectivity' if used in an adjunctive or triage mode.
5. Cost Effective Approach. In order to make an impact on cervical or other disease management, this new technology is economically viable in order to be accepted by potential users.

In the preferred embodiment we use both fluorescence and reflectance (multimodal) spectroscopy with visible and UV light though they can be used independently. Cervical cancer being an epithelial cancer provides an ideal target for diagnosis using both spectroscopic methods. This is because of the short path that light energy must travel (100 μm-1 mm) to fully penetrate the epithelium down to the germinative layer. Consequently, light undergoes minimum absorption and scattering from non-specific interactions while obtaining information on the biochemical and morphological state of tissue.

Both spectroscopic techniques may be used simultaneously in an imaging mode allowing the entire cervix to be interrogated if desired. Many investigators have pointed to the large patient-to-patient variation in the spectroscopic signature of normal tissue. This patient-to-patient variation is often higher than the variation between the spectroscopic signatures of normal and diseased tissue in the same patient. As a result, absolute intensities are of little value and it is necessary to baseline or normalize all measurements on a subject to those made on normal tissue in the same subject. It is this relative measure or change that has diagnostic relevance. Given the inherent inability to determine 'a priori' the location of abnormal and normal tissue with certainty, the logical alternative is to measure the entire cervix. So in short, it is preferably to measure a large portion of the cervix in order that a base line of normal tissue and be observed, interrogated and compared to other, potentially diseased tissue. Identifying healthy baseline tissue is achieved by 1) recognizing that it is likely that most of the cervix is healthy and thus by measuring all or large part of the cervix, the majority of tissue can be assumed to be healthy and 2) we have found that most abnormalities tend to spread vertically therefore, by scanning substantially horizontally, on most scans, we are likely to detect both healthy an diseased tissue in a most passes. This provides for easier differentiation and eliminates the problems with attempting to calibrate the system across patients, which is prone to significant error.

Possible measurements include: 1) blood profusion (angiogenesis), 2) epithelial thickening, 3) nuclear site and content, 4) cell orientation. In the preferred embodiment, the system (sensor) is non-contact. This has the significant advantage that the tissue is not disturbed in any way by contact with the system. Contact can dramatically skew the test results. Further, the preferred embodiment does not require the use of tissue preparation such as with acetic acid. Acetic acid pre-treatment of tissue will enhance detection of nuclear size and content, by increasing reflectance but tend to suppress all other test measurement mentioned above.

Fluorescence measurement. A fluorescence measurement is made by measuring the intensity of light emitted from the tissue at a wavelength red-shifted (longer) from that of light used to irradiate the tissue, and preferably filtering (blocking) the irradiation light frequencies). Fluorescence measures biochemical changes, i.e., the earliest changes that occur in the course of normal cells becoming malignant. The natural fluorophores present in tissue are the aromatic amino acids tyrosine, phenylalanine and tryptophan, the metabolites NAD(H), FAD and FAD(H) and structural proteins collagen and elastin. The fluorescence from these molecules depends upon their physiochemical environment including pH, solvation and oxidation state. For example, the reduced form NAD(H) fluoresces while the oxidized form does not. The reverse is true for FAD(H). The action of various proteases secreted by tumor cells on structural proteins renders the fluorophores (tryptophan, phenylalanine etc.) exposed to a different local environment (different solvation, viscosity and hydrophobicity), thus altering their fluorescence.

Reflectance measurement. This measurement is made by measuring the intensity of light returned from the tissue at the same wavelength as that used to irradiate the tissue. Reflectance measures the morphological changes associated with cancer progression. Although biochemical changes precede the morphological changes that occur as a result of the former, varying degrees of morphological change, in reality, accompany the biological changes. Morphological changes appear later in the course of tumor progression and are defined as any change in cell nuclei, cell size, cell appearance, cell arrangement and the presence of non native cells. In addition, effects of the host response such as increased perfusion from angiogenesis result in an overall difference in tissue appearance. The morphological changes add more complexity to the fluorescence measurement by scattering and absorbing both the excitation and fluorescent light thereby altering the true fluorescence signal. Thus, it is difficult to make a fluorescence measurement that is truly independent of the effects of scattering and absorbance.

Multimodal Spectroscopy. The interactive nature of the information gathered from fluorescence and reflectance modes makes it preferable to use both modes to correct for interferences from one mode to the other. For example, by knowing the absorption and scattering at each site on the tissue, the corresponding error that these effects produce in the fluorescence yield can be corrected for. In addition, as explained earlier, the information content of each mode is partly exclusive with fluorescence being sensitive to earlier biochemical changes and reflectance being sensitive to later morphological changes. Thus by combining the two modes a better measurement is made. This is the crux of the multimode spectroscopy advantage. In order to gain this advantage, however, both measurements must be made on the same site at preferably the same or nearly same time so as to ensure identical conditions.

In addition to detection, the present invention may include a camera (still and or video) and spectrograph together comprise the detection system.

Figure 25:
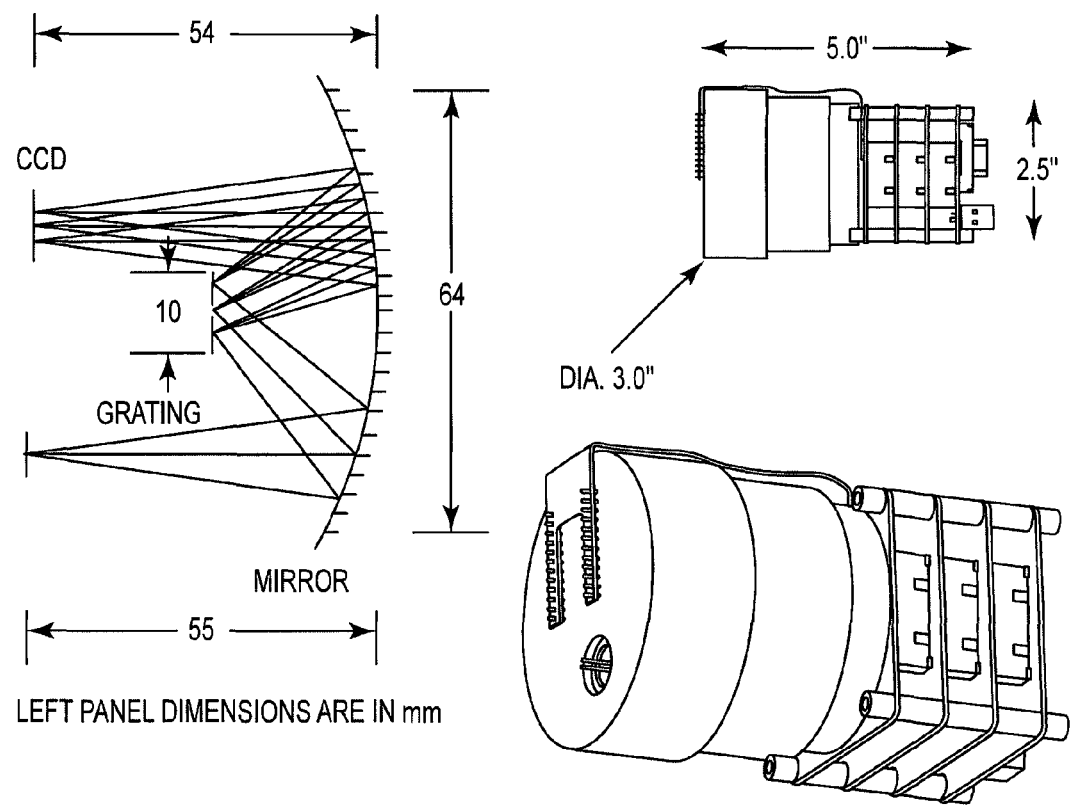
FIG. 25 is a view of an optical system of an alternative embodiment.

This integrated camera-spectrograph is shown in FIG. 25.

Layout of a preferred spectrographic system includes: convex aberration corrected grating and concave mirror. The entrance slit and the position of the CCD are as shown. (right panel) A CCD camera where the sensor is placed at the focus of the spectrograph as shown and analog data is carried to the A/D converter via a cable. The A/D converter is placed with the CCD preamplifier and clock driver on one of 4 boards modularized in order to provide flexibility of placement FIG. 25.

Figure 26:
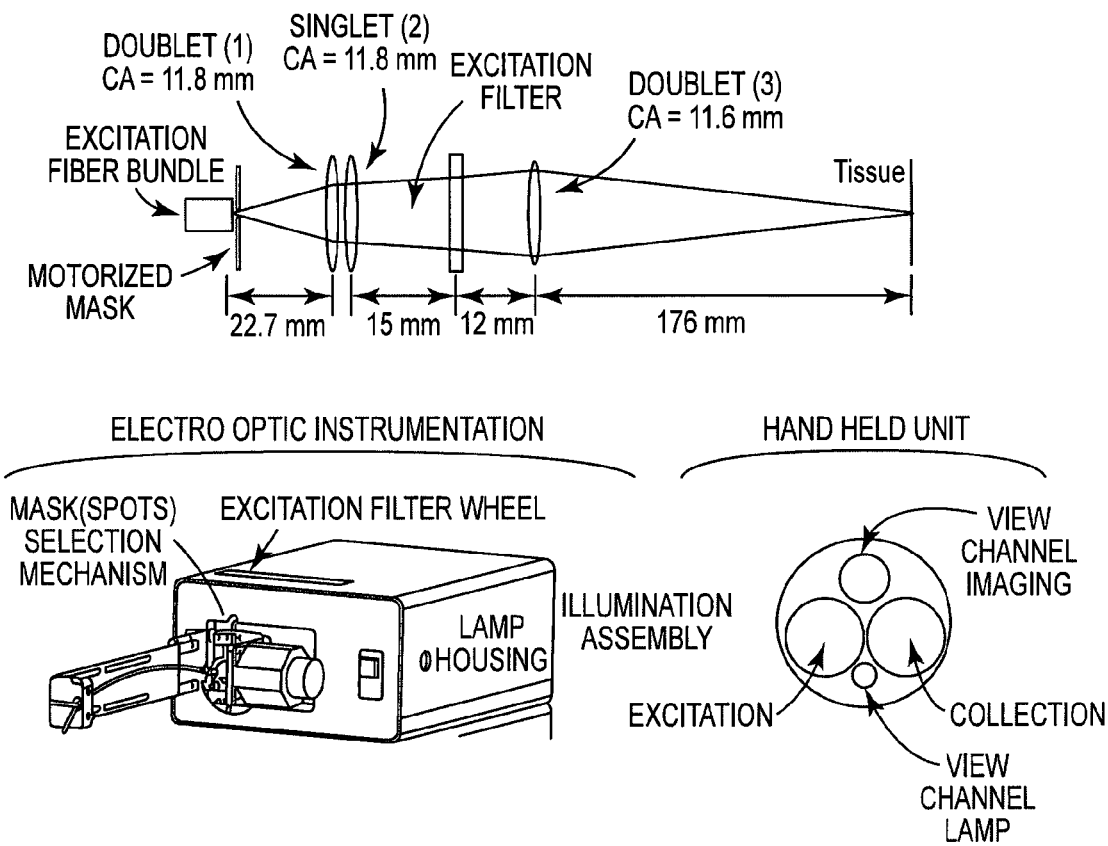
FIG. 26 is a schematic illustration of on embodiment having a coherent fiber bundle connecting the base and hand held units.

FIG. 26, this device includes two parts: (a) A hand held patient interface that is electrically and optically connected to (b) the electro-optic instrumentation located on a movable cart. The hand held unit (HHU) looks like a hair dryer and has a removable snout called the 'contact tube'. The contact tube is designed, in conjunction with a vaginal speculum, for placement in the patient's vagina during the examination procedure. Prior to subject measurement the instrument is calibrated by making measurements on fluorescent and reflective calibration targets.

FIG. 26 Simplified schematic of the research prototype showing key component details of a system with a coherent fiber optic bundle.

During probe insertion, the subject's cervix is illuminated by a small lamp and viewed through a video-imaging camera, both of which are located in the HHU. This camera provides a 'video view' of the subject's cervix on a monitor and assists the physician in properly aligning and positioning the contact tube and helps determine if there has been any movement during the test. The contact tube makes circumferential contact with the periphery of the cervix. The spectroscopic interrogation, however, is done in a stand-off manner on the area enclosed by the contact tube. After the contact tube is satisfactorily positioned, the video camera is used to capture a still image of the cervix, which is digitally stored and used for later data analysis. The video lamp is then automatically turned off and the spectroscopic measurement started.

Figure 27:
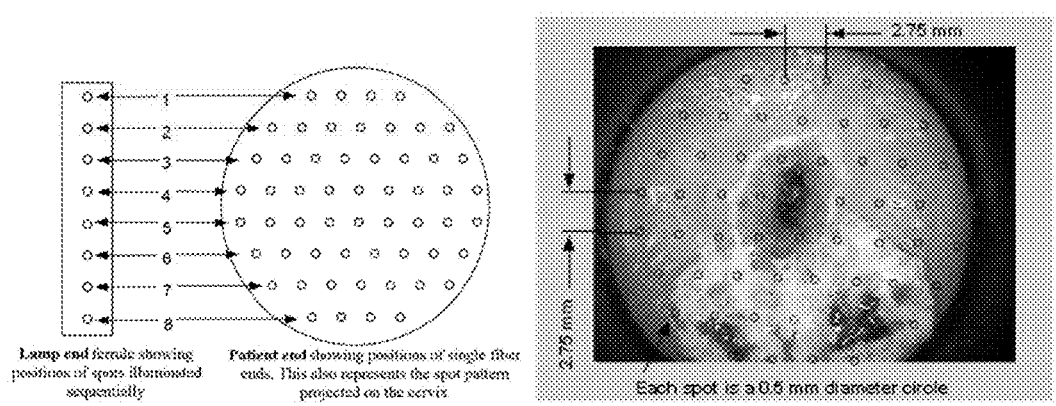
FIG. 27 is a pair of related images, the left being a schematic view of the points of interrogation and on the right, a photographic image of a diseased cervix with the point of interrogation overlayed such as with the composite presentation of the image and measurement systems herein.

FIG. 27 In one embodiment, illumination fiber bundle design showing how spots, representing multiple fibers each, at the lamp end map to corresponding columns at the patient end. Also shown is a view channel image of the cervix showing overlaid spots where the cervix is spectroscopically interrogated and the dimensions of the spots and the pattern. The cervix shown therein is a plastic medical replica of an average adult female.

The research prototype spectroscopically interrogates the cervix in a structured manner from a standoff distance of approx. 176 mm that is maintained by the length of the contact tube. Measurements are made of 56, 0.5-mm circular spots nominally separated from each other by 2.75 mm as shown in FIG. 4 and FIG. 5. We use the line scan approach to gather data from all 56 points. In this method a line or column of points is illuminated at any given time and the returned radiation from the tissue is collected using a coherent fiber bundle. In another embodiment, the coherent light bundle is dispensed with by moving the sensor to the HHU. This produces many advantages as will be explained below. The column of light is transferred through the coherent fiber bundle and acts as a virtual slit at the entrance of the spectrograph used to spectrally resolve the light. Given the spectral resolution required and the light dispersion by the spectrograph, only one column can be measured at a given time. The system sequentially scans through all eight rows shown in FIG. 27 and FIG. 28, acquiring both fluorescence and reflectance spectra in a total time duration of 4.5 minutes.

Figure 28:
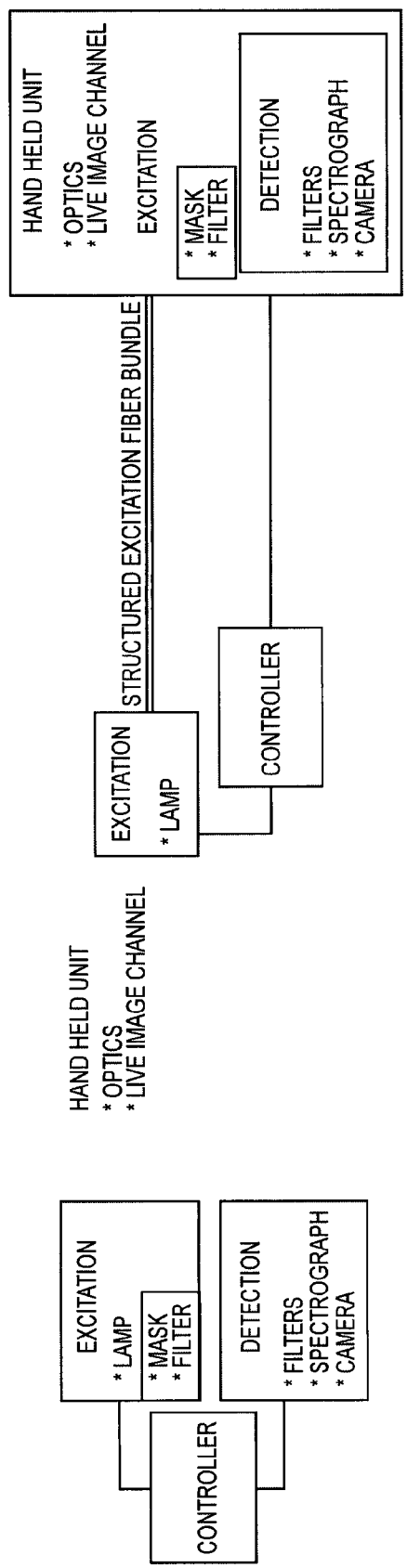
FIG. 28 shows three block components of the system. The middle block (Hand Held Unit) may be part of either the left or right hand block depending on the embodiment.

FIG. 28 shows a scanning method by which spots on tissue are illuminated and imaged (after spectral resolution) onto the CCD. The first row shows how a total of 56 spots are illuminated in a sequence of 8 shots. The actual sequence is different from that shown and is as follows: 4, 5, 3, 6, 2, 7, 1, 8 or an inside to outside horizontal scan pattern. Given that disease occurs primarily in the center of the field near the os and the squamo-columnar junction and extends when it does in a top to bottom direction, this scan pattern ensures that the center of the field is imaged first the likelihood of simultaneous sampling of both normal and diseased tissue is maximized. The bottom row shows how light from each row of spots after spectral decomposition is imaged on a rectangular portion of the CCD.

The components of one embodiment of the HHU are described below. The Contract tube snaps onto the HHU and serves as a light barrier to exclude room light, a channel for providing an unobstructed view of the cervix and fixes the object (cervix) distance from the lens assembly in the HHU to 176 mm, the focal length of the optics.

a) Video imaging camera. A ¼" format color CCD board camera is placed behind a dedicated lens set.
b) b) Lamp light source for video imaging: A 4.25 W halogen lamp with an integrated elliptical reflector is used with a GG295 filter (suppresses any energy less the 295 nm) to provide uniform illumination on the cervix for video viewing
c) Illumination fiber bundle. Illustrated in FIG. 27, this custom bundle accomplishes the line scan approach. It uses 56, 2 meter long, 0.12 NA, 100 µm core diameter fibers. Fibers from each one of eight rows at the patient end, maps to one of eight spots at the lamp end as shown. Lamplight (from the 300 W arc lamp described below) is sequentially coupled into one of the eight spots of the lamp end ferrule causing one column at the patient end to light up at a time.
d) Collection fiber bundle. This is another custom bundle that uses 0.43 NA, 2 meter long, 10 µm element fibers arranged in a 6×6-mm square aperture in a coherent fashion to provide a one to one image transfer from the HHU to the spectrograph. The spectrograph end is rotated 90° so that each row imaged at the patient end serves as a virtual column or slit at the entrance to the spectrograph.
e) Lens sets for excitation and collection. In order to focus the illumination for spectroscopy on the cervix and for collecting tissue emission a matched set of achromatic lens doublets is placed in front of the patient ends of the excitation and collection bundles respectively. The doublets are BK7/SF2 glass biconvex/planoconcave combinations. The material choice limits irradiation to greater than 300 nm and collection to greater than 400 nm.

Electro-Optic Instrumentation. The electro-optic instrumentation is located on a movable cart and consists of the illumination, detection, control instrumentation, user interface and data storage. The electro-optic instrumentation is further divided into illumination, detection and control subsystems.

The illumination subsystem: the following component are listed in their preferred order of appearance in the light path.

1. Lamp assembly. This is a 300 W short-arc Xe lamp with an integrated parabolic reflector, which produces a near collimated beam.
2. Hot mirror. The near collimated lamp light beam is directed at a "hot mirror" placed in the beam path. The mirror transmits wavelengths in the range of 250-700 nm and absorbs/reflects the IR wavelengths.
3. Motorized excitation filter wheel. This eight-position filter wheel is mounted inside the lamp enclosure as shown in FIG. 26. The filters used in each specific measurement are listed in Table 2.

TABLE 2

Spectral measurement parameters.

| # | Measurement | Excitation | Collection | Spectral Range | Measurement time |
|---|---|---|---|---|---|
| R | Reflectance | OD filter as needed | OD filter as needed to | 400-700 nm | 0.5 secs |
| F | Fluorescence | 340 nm (40 nm) | 385 nm Long-pass | 450-700 nm | 5 secs |
| F | Fluorescence | 400 nm (30 nm) | 435 nm Long-pass | 500-700 nm | 5 secs |
| F | Fluorescence | 460 nm (20 nm) | 495 nm Long-pass | 500-700 nm | 5 secs |

4. Motorized safety shutter. Although the lamp operates continuously, this shutter allows Illumination into the system and through to the patient only for the duration of the spectroscopic measurements.
5. Focusing lens. A custom built aspheric lens is used to focus light into the excitation fiber bundle.
6. Motorized mask. A custom designed mask that is actuated using an encoded stepper motor and controller translates the 'lamp end ferrule of the excitation bundle' to position each spot, as illustrated in FIG. 27, coaxially with respect to the lamp/lens illumination output.

The collection subsystem: The components are listed in the preferred order of appearance in the light path.

1. Collection filter wheel and re-imaging assembly. The collection wheel is populated with filters as listed in Table 2. The re-imaging assembly re-images the fiber column at the spectrograph entrance and corrects chromatic aberrations and astigmatism caused by the filters being present between the spectrograph and the detection end of the coherent bundle.
2. Imaging Spectrograph. The imaging spectrograph has a 300-mm focal length with a 40-lines/mm plane grating in a CzernyTurner arrangement. The spectrograph with this grating allows us to capture a spectral range of 885 nm.
3. CCD Camera. A thermoelectrically cooled CCD camera with a SITE 512×512, square format, 24 μm pixel, back illuminated detector along with the ST-133 high speed DMA serial interface controller. The A/D converter in the controller allows a 1.0 MHz A/D scan rate.

Key device features that determine data quality and device discrimination performance.

a. Spectroscopic measurements of the cervix while at a standoff from the cervix. Since the optical properties of tissue as well as the efficiency of light coupling into tissue are altered, standoff and contact measurements are qualitatively different.
b. Spectroscopic interrogation of 56 points on the cervix of spot size and spacing as shown in FIG. 27. Cross talk between spots illuminated simultaneously as well as the spatial resolution of the measurement is determined by this factor, which must be preserved.
c. Multimodal spectral measurement (1 reflectance and 3 fluorescence) at 10 nm spectral resolution as listed in Table 2. A key finding was that 10 nm was the optimal spectral resolution for best device performance. In addition spectral measurement parameters are as shown in Table 2 with the exception of measurement times as explained in item 'g' below.
d. A spectroscopy light source with an excitation spectrum of a typical Xenon arc lamp. This is necessary in order to preserve the relative intensities at each wavelength as well as use certain lamp spectral peaks for calibration purposes.
e. Include a video imaging channel. This is to facilitate proper positioning of the cervix in preparation for spectroscopy as well as to provide a color picture of the portion of the cervix that is the same as the portion measured spectroscopically. In addition the video imaging channel to be co-aligned with spectroscopy imaging channel (common image plane). The video/still image can be aligned and overlayed on the spectrographic analysis so that the user can identify visually where the system believes the abnormal tissue is located without further intervention. Furthermore, the system can take "before" and "after" still images and compare to insure that movement during the test was not so great as to compromise the test results. This could occur, for example if the contact tube is found to have moved from its initial position to its final position in the before and after images. This would suggest that during the tissue examination by the system, the tissue or system had moved.
f. Nominal and maximum power per spot. The nominal power per spot on tissue is listed in Table 3. The maximum exposure time can be increased 10×, across the board, without exceeding the safety thresholds specified by the American Conference of Governmental Industrial Hygienists (ACGIH). This provided the same exposure times listed are used. A shorter exposure time may permit higher power levels and will be prorated accordingly.

TABLE 3

Nominal power per spot measured on tissue for each excitation mode. The power should not drop to below 50% of the stated nominal power over the life of the device. The power levels indicated are irradiated over the integration times shown.

| Nominal Power on Cervix | 7.3 μW | 24.6 μW | 28.1 μW | 98 μW$^e$ |
|---|---|---|---|---|
| Exposure time | 5 secs | 5 secs | 5 secs | 0.5 secs | g. Measurement time. The measurement time for the research prototype is 4.5 minutes. This time is about equally distributed between actual CCD image acquisition time and time spent in moving stepper motors in preparation for the next measurement. While some reduction in the latter can be achieved by more efficient motion and control, the CCD integration time (measurement time in Table 3) as well as the digitization/data transfer time must also be reduced. We are capturing at least 36 images (8 mask positions×4 modes+4 dark images) and any reduction in image integration and transfer time would therefore be significant. We will have reduced image transfer time from 500 ms currently to 200 ms by using a faster A/D and camera interface in the JY camera. Integration time can be reduced by improving system throughput, a goal that is addressed for all components affecting throughput in this grant application.
h. Instrument Signal to Noise Ratio (SNR): The SNR is a performance metric that is partially affected by system throughput. An increase in throughput increases SNR. Given that our device is a multichannel instrument (measuring multiple spatial points simultaneously) the SNR is divided into two components as shown. The requirements shown are based on average results from multiple copies of the research prototype. We require that the performance of the pre-production device be equal to or higher than the numbers shown. Note that SNR is an issue for fluorescence measurements only. Reflectance measurements typically have an orders of magnitude higher SNR and therefore do not have an SNR problem. Any device changes that result in higher fluorescence SNR however, will also further increase reflectance SNR.

Single Channel SNR. The SNR over multiple (static) measurements of the same point at intensity levels measured on a temporally stable calibration target for 340, 400 and 460 nm fluorescence emissions.

$$SNR = \frac{\text{Mean of multiple intensities measured at a single point on a Calibration target}}{\text{Standard deviation of the same}} = 80 \pm 10$$

Multi-channel SNR. The SNR over all 56 points in a single measurement of a flat (spatially uniform) calibration target. This measurement is also made at intensity levels measured on tissue for 340, 400 and 460 nm fluorescence emissions.

$$SNR = \frac{\text{Mean of calibrated intensities from 56 points measured on a Calibration target}}{\text{Standard deviation of the same}} = 13 \pm 2$$

i. Human factors. Certain human factors related parameters based on marketing and human factors studies described in Sections 4.4.7 and 4.4.8, must be preserved as listed in Table 4.

TABLE 4

Key Human factor parameters

| | |
|---|---|
| 1. Weight of Hand Held Unit | 5 lbs |
| 2. Dimensions of HHU | Industrial design model is available and optimized for usability |
| 3. Length of Contact tube | 176 mm. |
| 4. Max diameter of contact tube at distal end | 1.14 inch. |
| 5. Length of Distal end. | 4 inch. |
| 6. Max diameter of contact tube at proximal end. | 1.26 inch. |
| 7. Length of proximal end | 2.8 inch (including step down to 1.26 inch at the distal end) |

FIG. 28 shows a functional block diagram of our research prototype. The base unit of this device contains the excitation and detection subsystems. The detection subsystem contains the spectrometer and camera, the cost and performance drivers of this device. They account for 65% of the overall device cost of the research prototype. Without a priori knowledge of the functional requirements of these two components, we chose a scientific grade state-of-the-art camera and spectrograph for the research prototype placing cost and size at a lower priority and deferring any effort to reduce cost and size to when functional requirements were known. In Phase I we will have designed, built and tested a size and cost reduced integrated camera-spectrograph allowing us to move it into the HHU (FIG. 28 right panel). As a result of this, we will be able to dispense with the coherent imaging bundle and the associated cost since we no longer need an image transfer mechanism. An immediate advantage of doing this is that our system throughput will be increased two-fold since the coherent bundle has a transmittance of 50%. Also as shown in Table 8, the device cost share of the camera and spectrograph is now reduced to 40%.

Figure 35:
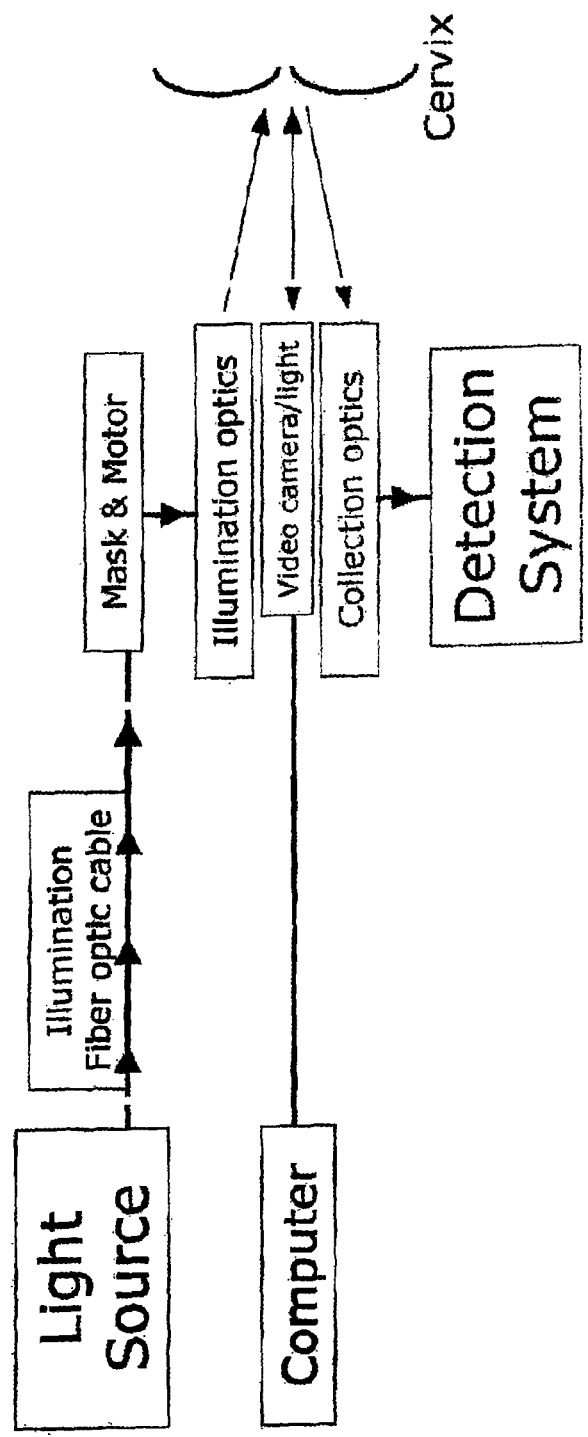
FIG. 35 is a schematic representation of the confocal arrangement of the excitation and collection/camera units.

FIG. 28 and FIG. 35 illustrate an alternative embodiments which may be preferred. The illustration on the left is a functional block diagram of the research prototype showing how the coherent imaging bundle connects the HHU to the detection subsystem in the base unit. In an alternative embodiment the detection subsystem is now placed in the HHU and we have dispensed with the coherent fiber bundle. The excitation filter wheel and mask assembly have also been transferred into the HHU. The items being relocated in the new design are shown in grey.

Figure 36:
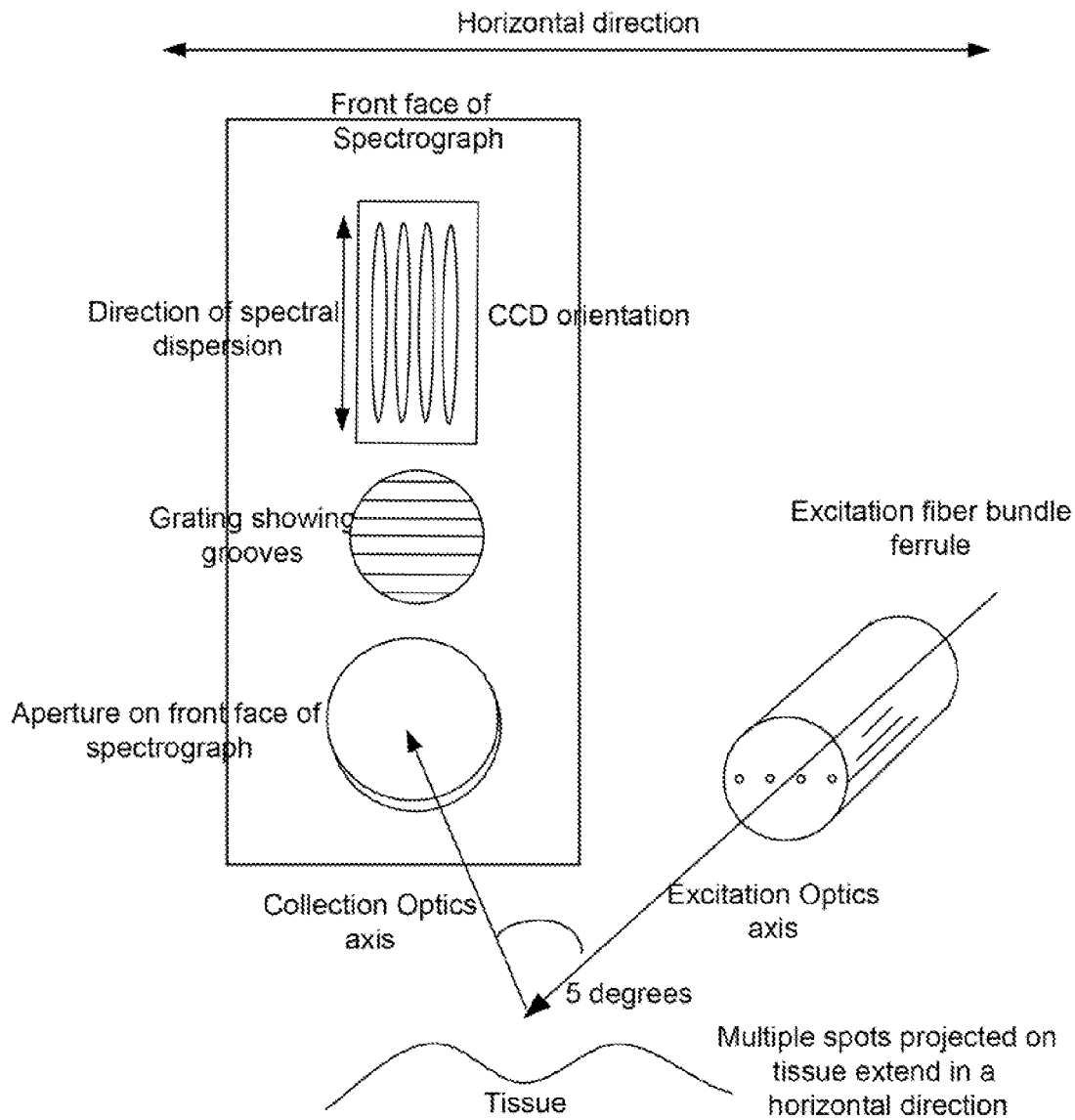
FIG. 36 is a schematic view of the system shown in FIG. 35 with the confocal arrangement of excitation and collection units at 5 degrees from each other.
Figure 37:
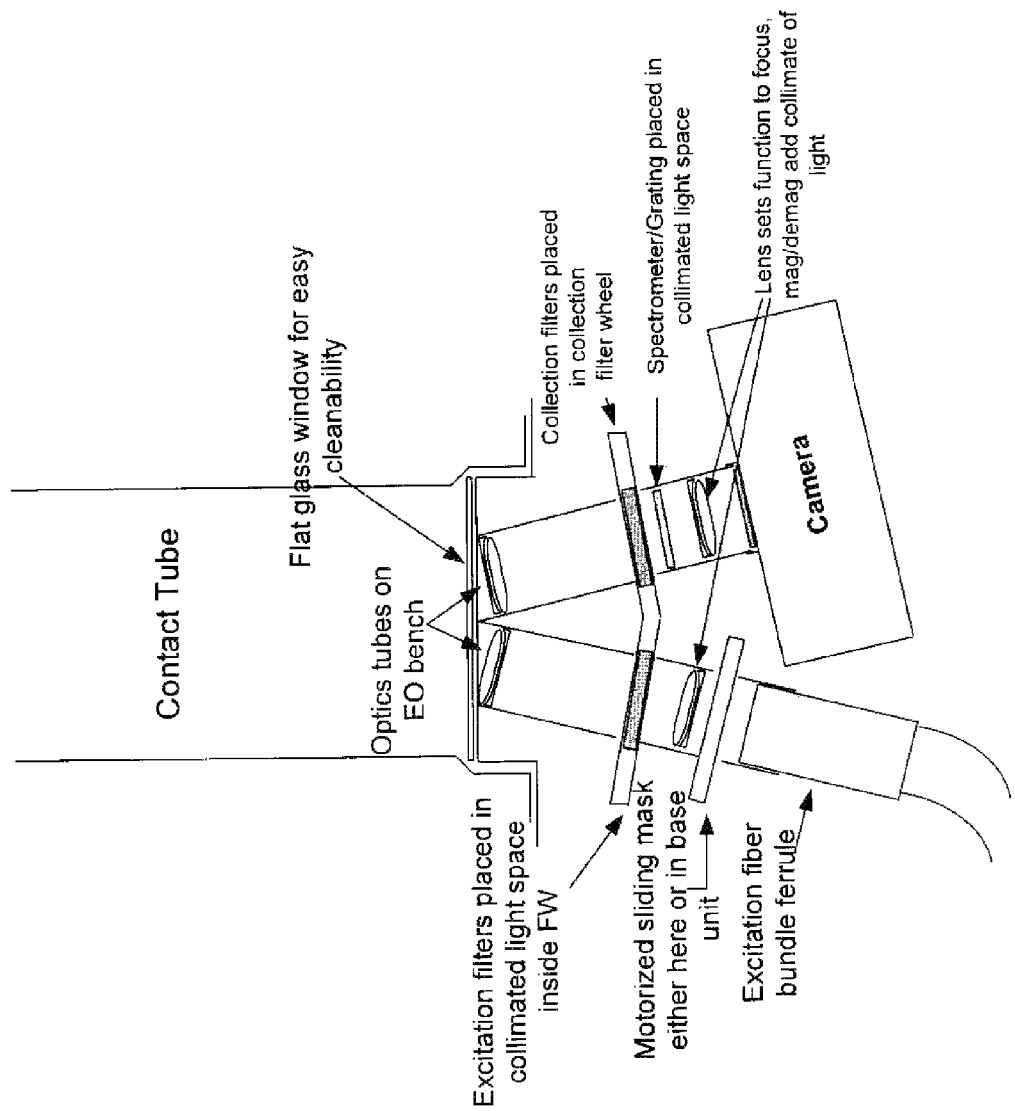
FIG. 37 is a diagramatic view of an improved embodiment where the hand held unit contains the mask, motor, illumination optics, video system, collection optics and detection system.

FIG. 36 is a schematic view of the system shown in FIG. 35 with the confocual arrangement of excitation and collection units at 5 degrees from each other;

FIG. 37 is diagramatic view of an improved embodiment where the hand held unit contains the mask, motor, illumination optics, video system, collection optics and detection system.

Excitation lamp and lamp housing. The excitation lamp used in the research prototype is a 300 W short-arc Xe lamp. This lamp uses bulb with an integrated parabolic reflector. A reduction in lamp power is desirable in order to have an inexpensive, compact, durable and rugged design with lower cooling demand. We, in our device, have an apparent trade off between lamp power and measurement SNR. An exception to this is to use a lamp with a geometry that allows for more efficient focusing of light into a given spot at a given Numerical Aperture (NA). This increases the energy coupled into the fibers at the lamp end of the excitation fiber bundle as illustrated in FIG. 29.

The excitation fibers are of a low Numerical Aperture or angle of light cone (NA) of 0.12. Maximizing low NA light coupling is important to match the low NA of the excitation optics in the HHU. The optics in turn use a low NA since a high NA is prone to stray light generation. Also our size constraints in the HHU require the use of small clear apertures (CA). All high NA light will be rejected by these optics and if present it will add to the stray light. We have used low NA fibers to reject high NA light at fiber entrance thus minimizing the generation of stray light in the optics. The disadvantage of a low NA is that the light throughput is lowered. This require a longer tissue examination, but elimination of the coherent fiber bundle provides such a dramatic improvement in the throughput, that the test time is actually shortened as seen in Table 6 below Excitation fiber bundle and mask assembly. There is the only fiber bundle that remains in the pre-production device design. Minimizing the use of fiber optics in a product is necessary for device ruggedness and for reducing the possibility of device damage from fiber breakage. For patient safety reasons the lamp, the only remaining key component, has been retained in the base unit and away from the patient. A fiber bundle is necessary to transfer light from the lamp in the base unit to the optics in the HHU. A six-foot length is required on this fiber bundle for HHU maneuverability and ease of use. We have to embodiments for this fiber bundle as illustrated in FIG. 29. Option 1 appears to be the preferred choice where both ends of the fiber bundle are fixed and a moving mechanical mask selects the rows of spots that are illuminated on tissue. The tradeoff is a lower power coupling per fiber as shown in Table 5. A stepper motor under software control will be used to move the mask. The structured end of the fiber bundle will be fixed in the HHU using appropriate strain relief. The mask and the mask stepper motor are both located in the HHU.

Figure 29:
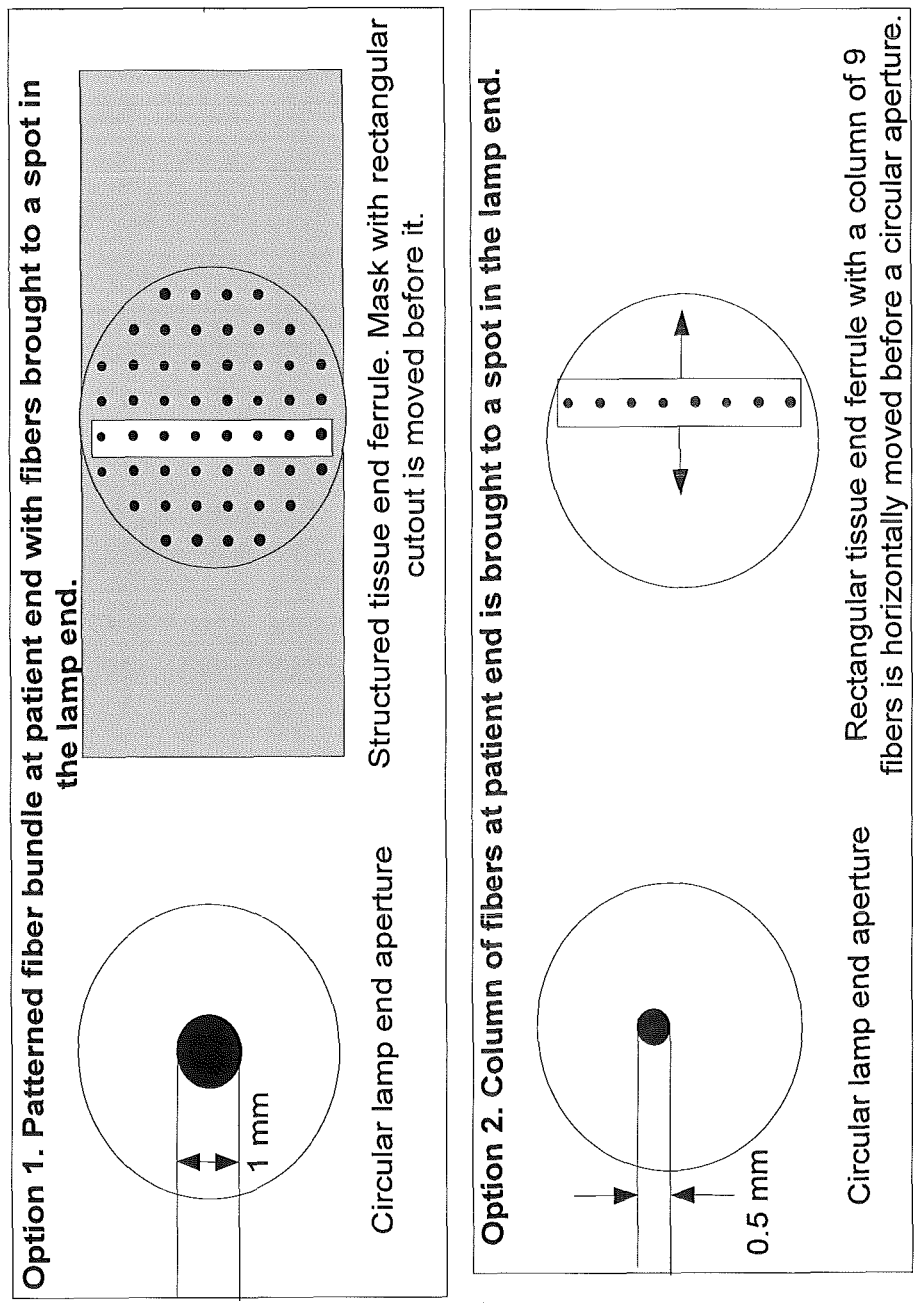
FIG. 29 shows a pair of schematic illustrations of the horizontal scanning of a plurality of vertical interrogation points.

FIG. 29. Excitation fiber bundle geometry options. In option 1 all 56, 100 μm diameter fibers are illuminated. In option 2 only 9 fibers are illuminated providing for a smaller spot diameter at the lamp end. However this option requires moving the fiber bundle ferrule in the HHU to scan the tissue.

Figure 30:
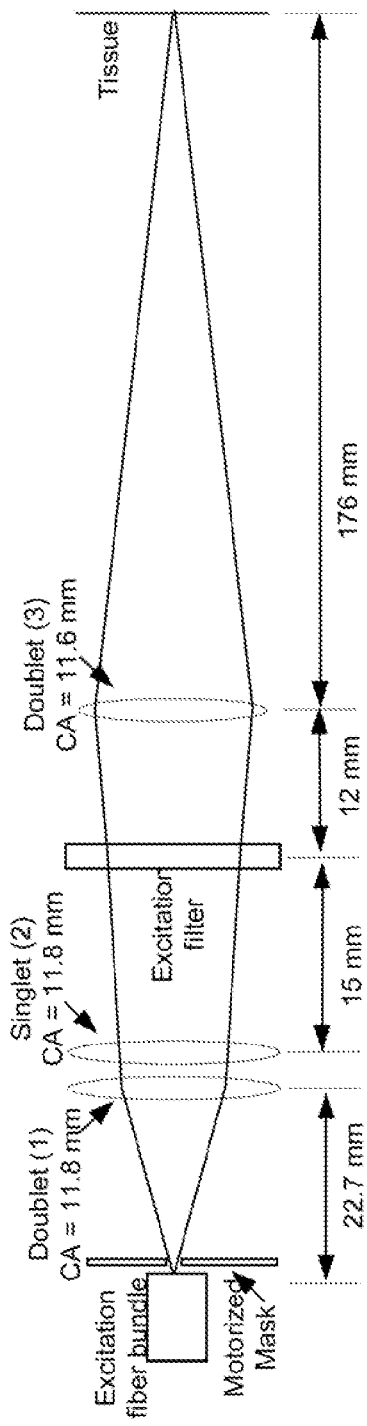
FIG. 30 is a schematic drawing of an optical system of a first embodiment.

Excitation Optics. The excitation optics is located in the HHU. These optics magnify and focus the spots of light produced by the excitation fibers onto cervical tissue. A preliminary design is illustrated in FIG. 30. The magnification factor chosen is 4.75 yielding nominally 500 μm spots on the tissue. A similar design is used in the existing research prototype. However, being limited to available off-the-shelf lenses, we suffered significant vignetting and transmittance loss which resulted in the excitation optics throughput being <60%. Vignetting is a particularly challenging issue that arises from our use of small lens clear apertures (CA) in order to meet the size constrains of the HHU. The design shown in FIG. 30 will use custom lenses and UV transmissive glass (Schott UBK7 glass). Custom lens prescriptions will also be optimized to reduce vignetting and thus increase throughput. The three lenses will be held in a 12 mm ID tube that is interrupted by a filter wheel (excitation FW) as shown. Zemax analyses have shown that it is possible to obtain a >90% throughput. In addition a low divergence beam will be maintained through the excitation band pass filters to eliminate wavelength shifts from non-normal light incidence. We will optimize the design to maintain a high spot size and intensity uniformity over the 25 mm diameter tissue as well as a depth of focus of +/−5 mm.

Figure 31:
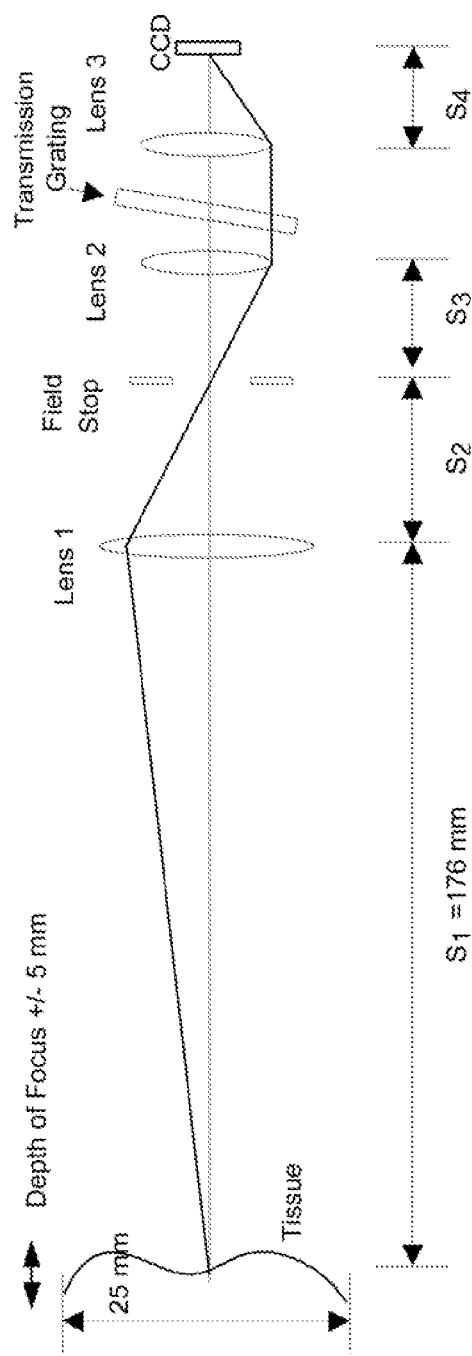
FIG. 31 is a schematic drawing of an optical system of a second embodiment.

Collection Optics. The collection optics is arranged alongside the excitation optics in the HHU in a confocal arrangement. The confocal arrangement makes it possible to locate the optics and sensors outside the patient yet in the hand held unit (HHU) and avoid the need for a coherent light fiber optic. The focus of both is at the tissue located 176 mm from the HHU and their primary axes form a 5 degree angle with respect to each other. A preliminary design is illustrated in FIG. 31. This is a design known as the Cooke triplet. The lenses are interspersed with a collection filter (collection filter wheel) and a grating for spectrally resolving the light. Early in our design efforts, we chose a transmission grating for spectral resolution as illustrated in FIG. 31. In the preferred embodiment we use a reflective grating for superior stray light performance. We show the transmission grating only to illustrate the design concept. Lens 1 demagnifies and projects an intermediate real image at a field stop. Lens 2 and 3 respectively serve to collimate (necessary prior to spectral splitting by the grating) and focus the spectrally resolved light on the CCD.

FIG. 31 shows a transmission grating, an option we previously considered. Although our current plan to use a reflective grating the figure serves to illustrate the Cooke Triplet design we have chosen.

Figure 32:
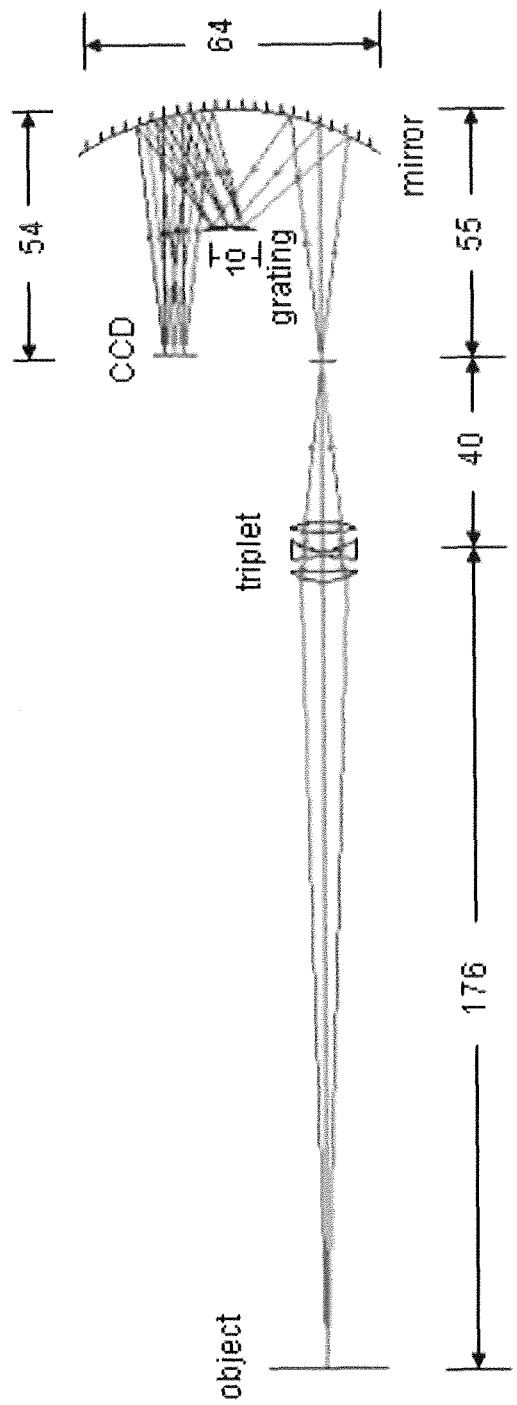
FIG. 32 is a schematic drawing of an optical system of the preferred embodiment with the system located in the Hand Held Unit.

In the reflective grating version, Lenses 2 and 3 are replaced by a single concave mirror that performs the same functions and images the field stop onto the CCD. The same design using a reflective grating is illustrated in FIG. 32. A triplet is chosen for lens 1 to correct for chromatic and geometric aberrations. The design shown is preliminary and has superior performance to that shown in FIG. 31 in terms of field distortion, stray light and cost.

FIG. 32 illustrate a Cooke triplet collection optics design using a reflective convex aberration corrected grating. Dimensions shown are in mm. The location of the field stop is as shown 40 mm to the right of the triplet. Clear Aperture of the triplet is to be determined.

Magnification. The image on tissue is demagnified (magnification=0.25) by lens 1 (triplet in FIG. 32). This demagnification is required and must be sufficient for spectra from all spots to be imaged within the dimensions of our chosen CCD. The CCD is chosen in the Phase I effort and subsequent design in Phase II is therefore dependent on this choice.

Intermediate real image at a field stop. This intermediate imaging is important since it allows the use of a spatial aperture that can be adjusted at the factory to eliminate any mirroring artifacts from the inside of the contact tubes. Although we will use a 'flat black' material for the contact tubes, some mirroring is expected and must be removed.

NA of light incident upon the CCD. The sensor chosen is an interline CCD with microlens integrated onto the silicon substrate. This limits the NA acceptance of the CCD with responsivity declining upon increasing NA. We chose an NA <0.2 where the responsivity is >80% of the maximum. This in turn limits the NA of light accepted onto the concave mirror at the field stop to <0.2. NA matching at the field stop is therefore important for both, maximizing throughput and minimizing stray light.

Video imaging Channel. The video imaging channel provides the user with feedback on proper device positioning on cervical tissue. It also allows the user to capture still images of tissue similar to those obtained by available video imaging colposcopes currently available. This feature will permit the procedure conducted with our device to be reimbursed using the colposcopy CPT code (please see market analysis in Table 7).

Figure 33:
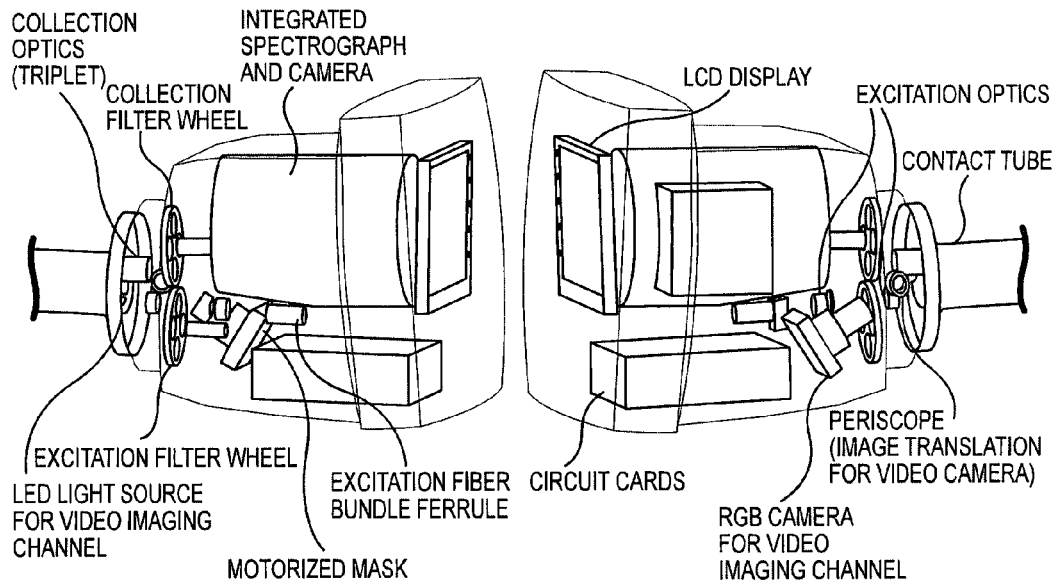
FIG. 33 is a CAD image of a Hand Held Unit taken from right and left sides (mirror images)

We have included this video imaging channel in the opto-mechanical layout of the pre-production HHU concept as illustrated in FIG. 33.

Optical throughput comparison. Among the key device requirements that determine data quality and discrimination performance are the following:

i. Maintain the nominal power per spot at or higher than those listed in Table 3.
ii. Maintain an instrument SNR (single and multi channel)
iii. Reduce measurement time to less than 3 minutes.

To illustrate this we conducted an optical throughput analysis using measured power and throughput efficiency for key optical components in the research prototype and compared these with those measured from the proposed components for the pre-production device as shown in Table 6.

The power in each fiber is taken from Table 5 (option 1 for one embodiment). The power at tissue is a measured value. This energy was reflected off a 10% reflective Spectrolon calibration target (Labsphere Inc. North Sutton, N.H.). Due to the lambertian reflectance profile from Spectrolon, which is similar to that off tissue, as well as the small aperture of the collection optics only 0.15% of the energy in each case is collected. This is a common problem in any tissue spectroscopy device and only a small fraction of energy emitted all around (in 4~steradians) is measured. We have assumed the same research prototype collection optics transmittance for both devices since the collection optics for the proposed device does not exist although we believe that transmittance in the design detailed in Section 4.4.4 will be higher and can be improved by using custom coatings and UV transmissive glasses. Our largest gains come from the elimination of the coherent bundle and the use of the integrated spectrograph design illustrated in FIG. 32. This results in a power at the CCD that is 10 fold higher than that currently seen in the research prototype. We can thus afford to lose some of this increase in power by reducing the CCD integration time, thus reducing the overall measurement time.

TABLE 6

Optical throughput comparison between the research prototype and the pre-production device. Starting with 460 nm (20 nm band pass) light coupled into a 100 μm excitation fiber and measuring the power exiting each component along the optical path we arrived at the power incident upon the CCD. Embodiment 2 shows a 10-fold increase in power arriving at the CCD compared to embodiment 1.
OPTICAL THROUGHPUT COMPARISON
460 nm excitation (20 nm band FWHM)
460 nm collection (20 nm band FWHM)

| Embodiment 1 (using coherent | |
|---|---|
| Power in each excitation FIBER (μW) | 28 |
| Excitation optics thruput (transmittance, vignetting) | 57% |
| Power at tissue (μW) | 16 |
| Target Reflectance (Spectralon) | 10% |
| Light gathering of collection optics | 0.15% |
| Collection optics throughput | 67% |
| Collection filter transmittance | 92% |
| Coherent bundle transmittance | 46% |
| NA missmatch at Spectrograph | 54% |
| Acton spectrograph transmittance | 32% |
| Power at CCD (nano W) | 0.12 |
| Embodiment 2 (no coherent bundle) | |
| Power in each excitation FIBER (μW) | 25 |
| Excitation optics thruput (transmittance, vignetting) | 90% |
| Power at tissue (μW) | 23 |
| Target Reflectance (Spectralon) | 10% |

TABLE 6-continued

Optical throughput comparison between the research prototype and the pre-production device. Starting with 460 nm (20 nm band pass) light coupled into a 100 μm excitation fiber and measuring the power exiting each component along the optical path we arrived at the power incident upon the CCD. Embodiment 2 shows a 10-fold increase in power arriving at the CCD compared to embodiment 1.
OPTICAL THROUGHPUT COMPARISON
460 nm excitation (20 nm band FWHM)
460 nm collection (20 nm band FWHM)

| | |
|---|---|
| Light gathering of collection optics | 0.15% |
| Collection optics throughput | 67% |
| Collection filter transmittance | 92% |
| Reflective spectrograph transmittance | 60% |
| Power at CCD (nano W) | 1.25 |

Figure 34:
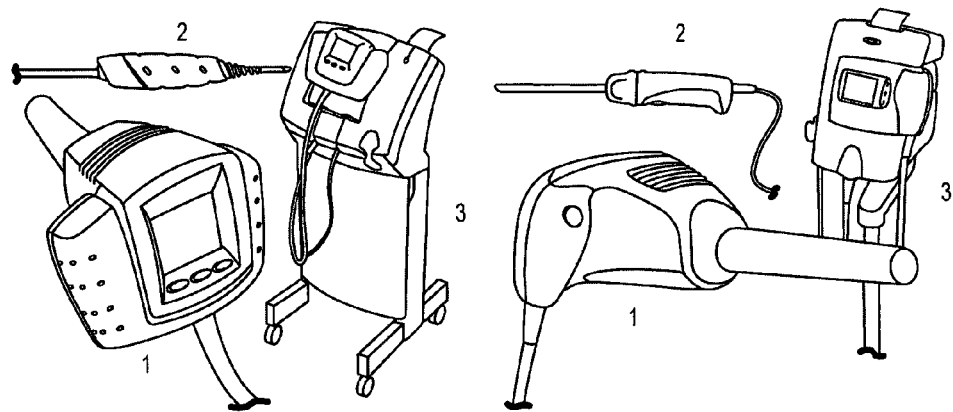
FIG. 34 is a CAD representation of a commercial unit of base, hand held unit and probe.

The ectocervical probe (component 1 in FIG. 34) contains a single-use contact tube (the black cylinder) that is positioned to contact the patient's cervix. It is shown as conical but could be tapered so long as it is not less that the system NA so that it does not impinge on the cone of light. The contact tube ensures proper positioning of the cervix relative to the optics in the probe body, attenuates ambient light sources, contains an integral calibration standard used to calibrate the instrument prior to patient measurements, and prevents cross-contamination between patients. The back of the ectocervical probe contains the controls and display used to operate the instrument. The endocervical probe (component 2 in FIG. 34) is a separate, slender probe that it used to measure the endocervical tissue. A single-use protective sheath is placed over the probe prior to measurement to prevent cross-contamination. The base unit (component 3 in the FIG. 34) contains common electronics, power supplies, light sources, printer, etc.

The following method may be used to perform a measurement.

1) Attach a new disposable contact tube to the ecto-cervical hand held unit (HHU) and enter patient data via the controls on the back of the ecto-cervical HHU. At this point, an automatic calibration is performed using a disposable calibration standard attached to the contact tube.
2) Remove and discard the calibration material from the contact tube.
3) Gently press the contact tube against the cervix by placing it inside a standard vaginal speculum that is already positioned inside the patient. The operator is aided in this positioned step by viewing a live video image of the cervix on the display on the back of the ecto-cervical HHU. Once the probe is properly positioned, the instrument automatically scans the cervix and collects the spectroscopic data in approximately three to four minutes.
4) Remove the ecto-cervical HHU from patient, remove and discard the contact tube, and place the HHU back in the base unit.
5) If an endo-cervical canal measurement is desired, place a new protective sheath on the endo-cervical probe and gently insert the probe into the patient's endo-cervical canal. Hold the probe in place for approximately one minute while the instrument collects spectroscopic data. Still and video images may be taken and the test will be run with a final still image preferably taken at the end of the test. When the data collection is complete, remove the probe, discard the sheath, and place the probe in the base unit.
6) The instrument automatically displays the test results on the ecto-cervical probe display and optionally prints a hardcopy on the printer. Results are shown using a numerical scale that ranges from 0 to 100, with higher values indicating greater probability of CIN2+ cervical disease. The device will also display a disease localization map, which will used a color coding to indicate areas on the cervix with of highest likelihood of having CIN2+ cervical disease. The map may be overlayed on to the still or video images which have been taken.

The continuous output scale displayed to the physician will be evaluated at two thresholds in order to determine sensitivity for detecting CIN2+ cervical disease and specificity for ruling out benign lesions on the cervix.

The foregoing embodiments and advantages are merely exemplary and are not to be construed as limiting the present invention. The present teaching can be readily applied to other types of apparatuses and applications that may be common to those of ordinary skill in the art. The description of the present invention is intended to be illustrative, and not to limit the scope of the claims. Many alternatives, modifications, and variations will be apparent to those skilled in the art. In the claims, means-Plus-function clauses are intended to cover the structures described herein as performing the recited function and not only structural equivalents but also equivalent structures.

What is claimed is:

1. An apparatus for determining tissue characteristics which indicate the presence of cancerous or pre-cancerous tissue on a body, comprising: a base unit comprising an illumination unit, a separate tissue interface unit comprising an excitation unit for delivering illumination from the illumination unit to the tissue and a detection unit capable of detecting responses in the tissue resulting from the illumination, said excitation and detection units being confocal and facing the tissue from the same side so that they converge at the tissue, a fixation member of predetermined length interposed between said units and the tissue to maintain alignment and focus with the tissue, said detection unit being aligned to maintain the detection unit and tissue in a substantially fixed position relative to each other as successive responses are detected despite natural movement of the body with respect to the detection unit and wherein the illumination unit comprises an illumination source and an illumination filter said filter configured to reduce artifacts due to reflected excitation, at least one filtration selected to enhance detection of reflectance and at least one filtration being selected to enhance detection of fluorescence and wherein the illumination unit further comprises a mask that provides for selective illumination of the target tissue, said mask including a generally horizontally oriented aperture allowing light transmission therethrough while blocking all other transmission, so that a column of a plurality of points in a single horizontal line of illumination can be applied simultaneously to the target tissue and thereby more easily distinguish between normal and abnormal tissue.

2. The apparatus according to claim 1, wherein said fixation member includes a hollow stand off tube having an outer peripheral contact edge bounding a hollow interior, said tube being, configured to space the separate tissue interface unit a predetermined distance from the tissue so that the portion of the tissue within the interior is not in contact with the tissue interfaces unit and therefore its optical characteristics are not affected by the detection unit.

3. The apparatus of claim 1 wherein said illumination and detection units are spaced from the tissue by a stand off tube and further-including an imaging device capable of recording images of the tissue and wherein said detection unit is confocal with said image device, so that the image of said image unit can be spacially correlated with data from said detection unit and whereby said tube maintains said unit and image device at a fixed distance from the tissue.

4. The apparatus according to claim 2 wherein said stand off tube is large enough to surround the target tissue without interfering with its optical properties.

5. The apparatus according to claim 2 wherein said target tissue is a cervix and wherein outer peripheral contact edge of said stand off tube is sized to be of equal or larger diameter relative to the target tissue size, so that none of the target tissue is blanched by contact with the contact tube.

6. The apparatus according to claim 1, wherein said filter has a plurality of filters selected to reduce artifacts due to reflected excitation is rotatable in sequence.

7. The apparatus according to claim 1, wherein said slit is configured to move generally in steps vertically, thereby creating a plurality of discrete horizontal row measurement across target tissue.

8. The apparatus according to claim 1 wherein the detection unit includes detection points arranged into a line of discrete points spaced from each other, so that detection of the tissue is done in a line of discrete separated detection points.

9. The apparatus according to claim 1, further including a diffraction grating for receiving and resolving light received from the target tissue into spectra of different wavelengths that extend orthogonally away from the column whereby the intensity of the light detected is indicative of the intensity at a different wavelengths.

10. A method of making time successive measurements of cervical target tissue while minimizing movement and the affects of movement of the target tissue during a measurement of tissue characteristics, comprising the steps of: a) contacting the tissue with a hollow tube around the periphery of the cervix without substantially contacting the cervical target area said hollow tube having one end in contact with the tissue and the other end being connected to an interrogation device, so that the optical characteristics of the tissue are not affected by the tube or the detection unit, b) forming a first image of the target tissue; c) illuminating a target tissue with optical energy; d) performing spectroscopic measurements on optical energy received from the target tissue from illumination sequentially in the form of a plurality of adjacent measurement taken sequentially across the target tissue.

11. The method of claim 10, further including the steps of e) forming a second image of the target tissue, f) comparing the first and second images to determine the degree of movement of the tissue, if any; g) comparing the degree of movement to a predetermined standard; h) if the movement is less than said standard, determining tissue characteristics of the target tissue based on the results of the spectroscopic measurements and wherein the step of performing spectroscopic measurements includes illuminating a first portion of a target tissue with optical energy from a first illumination source and illuminating a second portion of the target tissue with optical energy from a second illumination source.

12. A method of determining locating and differentiating normal and abnormal cervical tissue by optical interrogation of target tissue comprising the steps of:
   a) illuminating a portion of the target tissue in a structured pattern as follows:
   1. illuminating a band of spaced apart, generally horizontal line of detection points and measuring optical energy received from said points,
   2. shifting said line of points generally vertically,
   3. illuminating a new portion of the target tissue, vertically offset from the previous illumination, sufficiently offset to prevent cross talk between adjacent lines, and
   4. measuring optical energy received from said points, to create a matrix of measured points
   5 determining the presence of abnormal tissue by comparing the returned optical energy from adjacent measured horizontal and vertical points by creating applying the optical energy to a diffraction grating, thereby creating first order spectra for measured points, determining which tissue are abnormal by comparing spectral characteristics of vertically adjacent points based on the assumption that abnormal tissue is more likely to spread vertically than horizontally.

13. The method of claim 12 further including the step of structured illumination includes masking a portion of the illumination so that only one line is illuminated at a time.

14. The method of claim 12 further including the step of structured illumination includes masking a portion of the illumination so that only one line is illuminated at a time and wherein the making is sequentially moved to sequentially illuminate adjacent lines.

15. The method of claim 14 further including the step of sequentially applying filters in the path of the illumination to sequentially measure different optical characteristics including reflectance and florescence.

16. The method of claim 12 further including determining tissue characteristics of the target tissue based on the results of the spectroscopic measurements including the step detecting tissue characteristics using the rule that the adjacent horizontal points are more likely to be the boundary between normal and abnormal tissue than adjacent vertical points.

17. The method of claim 12, wherein the plurality of detection points are separated from each other sufficiently minimize crosstalk between points.

18. The method of claim 12, further including the step of surrounding the periphery of the tissue without contacting the target area with a hollow tube having one end in contact with the tissue and the other end being connected to an interrogation device.

19. The method of according to claim 12, further including the set of spreading light orthogonally to the angle of incidence thereby resolving light received from the target tissue in spectra of different wavelengths whereby the intensity of the light detected is indicative of its intensity at a different wavelengths.

20. The method of claim 12 wherein said diffraction grating creates elongated first order spectra which data is captured according to frequency and intensity.

* * * * *